US008728516B2

(12) United States Patent
Catron et al.

(10) Patent No.: US 8,728,516 B2
(45) Date of Patent: May 20, 2014

(54) STABILIZED LIPID FORMULATION OF APOPTOSIS PROMOTER

(75) Inventors: Nathaniel Catron, Vernon Hills, IL (US); Michael G. Fickes, Evanston, IL (US); Cristina M. Fischer, Wadsworth, IL (US); Anthony R. Haight, Wadsworth, IL (US); Katherine Heemstra, Chicago, IL (US); Yeshwant D. Sanzgiri, Gurnee, IL (US); Eric A. Schmitt, Libertyville, IL (US); Ping Tong, Libertyville, IL (US); Geoff G. Z. Zhang, Libertyville, IL (US); Deliang Zhou, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 343 days.

(21) Appl. No.: 12/770,174

(22) Filed: Apr. 29, 2010

(65) Prior Publication Data

US 2010/0278905 A1    Nov. 4, 2010

Related U.S. Application Data

(60) Provisional application No. 61/289,254, filed on Dec. 22, 2009, provisional application No. 61/174,299, filed on Apr. 30, 2009.

(51) Int. Cl.
*A61K 9/48* (2006.01)

(52) U.S. Cl.
USPC ........................................................ 424/451

(58) Field of Classification Search
None
See application file for complete search history.

(56) References Cited

U.S. PATENT DOCUMENTS

| | | | |
|---|---|---|---|
| 5,536,729 A | 7/1996 | Waranis et al. | |
| 5,538,737 A | 7/1996 | Leonard et al. | |
| 5,559,121 A | 9/1996 | Harrison et al. | |
| 5,635,187 A | 6/1997 | Bathurst et al. | |
| 5,645,856 A | 7/1997 | Lacy et al. | |
| 5,665,379 A * | 9/1997 | Herslof et al. | 426/450 |
| 5,707,648 A | 1/1998 | Yiv | |
| 6,004,973 A | 12/1999 | Guitard et al. | |
| 6,267,985 B1 | 7/2001 | Chen et al. | |
| 6,309,663 B1 | 10/2001 | Patel et al. | |
| 6,451,339 B2 | 9/2002 | Patel et al. | |
| 6,464,987 B1 | 10/2002 | Fanara et al. | |
| 6,964,946 B1 * | 11/2005 | Gutierrez-Rocca et al. | 514/4.4 |
| 7,459,283 B2 | 12/2008 | Wertz et al. | |
| 7,842,681 B2 | 11/2010 | Elmore et al. | |
| 7,973,161 B2 | 7/2011 | Bruncko et al. | |
| 8,168,784 B2 | 5/2012 | Franczyk, II et al. | |
| 2002/0055631 A1 | 5/2002 | Augeri et al. | |
| 2003/0236236 A1 | 12/2003 | Chen et al. | |
| 2005/0101628 A1 | 5/2005 | Jiao et al. | |
| 2005/0163835 A1 | 7/2005 | Gellert et al. | |
| 2005/0208082 A1 | 9/2005 | Papas et al. | |
| 2006/0177430 A1 | 8/2006 | Bhushan et al. | |
| 2006/0183776 A9 | 8/2006 | Pratt | |
| 2007/0027135 A1 * | 2/2007 | Bruncko et al. | 514/211.15 |
| 2007/0072860 A1 | 3/2007 | Bruncko et al. | |
| 2007/0104780 A1 * | 5/2007 | Lipari et al. | 424/456 |
| 2007/0161681 A1 * | 7/2007 | Marfat et al. | 514/338 |
| 2007/0243257 A1 | 10/2007 | Bedos et al. | |
| 2008/0085313 A1 | 4/2008 | Given et al. | |
| 2008/0182845 A1 | 7/2008 | Bardwell et al. | |
| 2009/0149461 A1 | 6/2009 | Krivoshik | |
| 2010/0233251 A1 * | 9/2010 | Von Andrian et al. | 424/450 |
| 2010/0278905 A1 | 11/2010 | Catron et al. | |
| 2010/0278921 A1 | 11/2010 | Fischer et al. | |
| 2010/0297194 A1 | 11/2010 | Catron et al. | |
| 2010/0305122 A1 | 12/2010 | Bruncko et al. | |
| 2010/0305125 A1 | 12/2010 | Borchardt et al. | |
| 2010/0323020 A1 | 12/2010 | Gokhale et al. | |
| 2011/0071151 A1 | 3/2011 | Zhang et al. | |

FOREIGN PATENT DOCUMENTS

| | | |
|---|---|---|
| CN | 1561201 A | 1/2005 |
| CN | 1706371 A | 12/2005 |
| CN | 101175738 A | 5/2008 |
| CN | 101220008 A | 7/2008 |
| CN | 101325944 A | 12/2008 |
| CN | 101798292 A | 8/2010 |
| EP | 1880715 A1 | 1/2008 |
| WO | 0057854 A2 | 10/2000 |
| WO | 0100175 A1 | 1/2001 |
| WO | 0224636 A2 | 3/2002 |
| WO | 03028705 A1 | 4/2003 |
| WO | 2005049593 A2 | 6/2005 |
| WO | 2007040650 A2 | 4/2007 |
| WO | 2007043057 A2 | 4/2007 |
| WO | 2008124878 A1 | 10/2008 |
| WO | 2009073835 A1 | 6/2009 |
| WO | WO2009073835 A1 | 6/2009 |
| WO | 2009155386 A1 | 12/2009 |

(Continued)

OTHER PUBLICATIONS

Wendt et al. (Expert Opin. Drug Discov. (2008) 3(9):1123-1143).*
Trotta et al. (European Journal of Pharmaceutics and Biopharmaceutics 53 (2002) 203-208).*
Bruncko M., et al, "Studies leading to potent, dual inhibitors of Bcl-2 and Bcl-xL" Journal of Medicinal Chemistry, 2007, 50 (4), 641-662.
Hanahan D., et al., "The Hallmarks of Cancer", Cell, 2000;100: pp. 57-70.
Hovorka S.W., et al., "Oxidative degradation of pharmaceuticals: Theory, mechanisms and inhibition", Journal of Pharmaceutical Sciences, 2001; 90 (3): 253-269.
Kibbe A.H., ed., Handbook of Pharmaceutical Excipients, 3rd edition. American Pharmaceutical Association, 2000, Table of Contents.

(Continued)

*Primary Examiner* — Brian Gulledge
*Assistant Examiner* — Snigdha Maewall

(57) ABSTRACT

An orally deliverable pharmaceutical composition comprises a Bcl-2 family protein inhibitory compound, e.g., ABT-263, a heavier-chalcogen antioxidant and a substantially non-aqueous lipid carrier, wherein said compound and said antioxidant are in solution in the carrier. The composition is suitable for oral administration to a subject in need thereof for treatment of a disease characterized by overexpression of one or more anti-apoptotic Bcl-2 family proteins, for example cancer.

4 Claims, 2 Drawing Sheets

(56) References Cited

FOREIGN PATENT DOCUMENTS

| | | |
|---|---|---|
| WO | 2010127190 A1 | 11/2010 |
| WO | 2010127198 A1 | 11/2010 |
| WO | 2011034934 A1 | 3/2011 |

OTHER PUBLICATIONS

Sutton V.R., et al. "Bcl-2 prevents apoptosis induced by perforin and granzyme B, but not that mediated by whole cytotoxic lymphocytes", Journal of Immunology, 1997, 158 (12), pp. 5783-5790.
Tse et al., "ABT-263: A Potent and Orally Bioavailable Bcl-2 Family Inhibitor," Cancer Research , 2008, 68 (9), pp. 3421-3428.
Anonymous: "Phosal(TM) 53 MCT"[Online] Feb. 2007, XP002601344 Phospholipid GmbH—American Lecithin Retrieved from the Internet: URL:http://www.americanlecithin.com/TDS/TDS_53MCT.PDF.
Park C.M., et al., "Discovery of an orally bioavailable small molecule inhibitor of prosurvival B-cell lymphoma 2 proteins," Journal of Medicinal Chemistry, 2008, 51 (21), 6902-6915.
PCT International Search Report for the Application No. PCT/US2010/033075, dated Oct. 19, 2010, 3 pages.
Berge et al., "Pharmaceutical Salts," Journal of Pharmaceutical Sciences, 66(1):1-19 (Jan. 1977).
Brandrup et al., "Polymer Handbook," 2nd Ed., John Wiley & Sons, 1975.
Caira, "Crystalline Polymorphism of Organic Compounds," Topics in Current Chemistry, 198:163-204 (1998).
Fiedler H. B., Encyclopedia of Excipients: For Pharmaceuticals, Cosmetics and Related Areas (Der Pharmazeutische Betrieb), 5th Edition, Editio-Cantor 2002.
Gould, "Salt selection for basic drugs," International Journal of Pharmaceutics, 33(1-3):201-217 (Nov. 1986).
Lessene et al., "BCL-2 family antagonists for cancer therapy," Nature Reviews, Drug Discovery 7:989-1000 (Dec. 2008).
Sperling L.H., Introduction to Physical Polymer Science, 2nd Edition, John Wiley & Sons (1992).
Brittain et al., "Effects of pharmaceutical processing on drug polymorphs and solvates," Polymorphism in Pharmaceutical Solids, 1999, vol. 95, pp. 331-361.
Chawla et al., "Polymorphism of pharmaceuticals: Challenges and opportunities," Article, Oct. 23, 2003, 3 pages, www.expresspharmaonline.com/20031023/edito2.shtml.
Crowley et al., "Pharmaceutical Applications of Hot-Melt Extrusion: Part 1," Drug Development and Industrial Pharmacy, vol. 33, 2007, pp. 909-926.
Holzelova et al., "Autoimmune Lymphoproliferative Syndrome with Somatic Fas Mutations," The New England Journal of Medicine, vol. 351, 2004, pp. 1409-1418.
International Search Report and Written Opinion of the International Searching Authority mailed on Dec. 13, 2010 regarding PCT/IB2010/001659 dated Dec. 13, 2010; 12 pages.
International Search Report for Application No. PCT/US2010/033072, mailed on Jul. 12, 2010, 4 pages.
International Search Report for Application No. PCT/US2010/033073, mailed on Oct. 8, 2010, 4 pages.
International Search Report for Application No. PCT/US2010/033074, mailed on Oct. 19, 2010, 4 pages.
International Search Report for Application No. PCT/US2010/033085, mailed on Oct. 19, 2010, 4 pages.
International Search Report for Application No. PCT/US2010/038526, mailed on Nov. 5, 2010, 4 pages.
International Search Report for Application No. PCT/US2010/048949, mailed on Nov. 30, 2010, 6 pages.
International Search Report for Application No. PCT/US2010/061588, mailed on Feb. 18, 2011, 3 pages.
Klein et al., "The Tablet Formulation of Lopinavir/Ritonavir Provides Similar Bioavailability to the Soft-Gelatin Capsule Formulation With Less Pharmacokinetic Variability and Diminished Food Effect," Journal of Acquired Immune Deficiency Syndromes, 2007, vol. 44; pp. 401-410.
Lessene et al., "BLC-2 family antagonists for cancer therapy," Nature Reviews / Drug Discovery, Dec. 2008, pp. 989-1000 , vol. 7, Macmillan Publishers Limited.
Moschwitzer et al., "Development of an intravenously injectable chemically stable acqueous omeprazole formulation using nanosuspension technology," European Journal of Pharmaceutics and Biopharmaceutics, vol. 58, Issue 3, Nov. 2004, pp. 615-619.
Paolini et al, Global mapping of pharmacological space, Nature Biotechnology, Jul. 2006, pp. 805-815, vol. 24, No. 7, Nature Publishing Group (http://www.nature.com/naturebiotechnology).
Puck et al., "Immune Disorders Caused by Defects in the Caspase Cascade," Current Allergy and Asthma Reports, vol. 3, 2003, pp. 378-384.
Rengan et al., "Actin cytoskeletal function is spared, but apoptosis is increased, in WAS patient hematopoietic cells," Blood, vol. 95 (4) 2000, pp. 1283-1292.
Sharma et al., "Solubility Enhancement Strategies for Poorly Water-Soluble Drugs in Solid Dispersions: A Review," Asian Journal of Pharmaceutics, 2007,vol. 1 (1), pp. 9-19.
Shimazaki et al., "Evaluation of apoptosis as a prognostic factor in myelodysplastic syndromes," British Journal of Haematology, vol. 110, 2000, pp. 584-590.
SkypePharma, DissoCubes [online], 2010 [retrieved on Nov. 17, 2012]. 1 page. Retrieved from the Internet: <URL: http:/ /www.skyepharma.com/T echnology/Oral_ Technology/Particle_Engineering_ Technologies/DissoCubes/Defau lt.aspx?id=81 >.
Sophie et al., "Synthesis of "Trioxaquantel" Derivatives as Potential New Antischistosomal Drugs," European Journal of Organic Chemistry, 2008, pp. 895-913.
Supplemental International Search Report and Written Opinion of the International Searching Authority mailed on Sep. 29, 2011 regarding PCT/IB2010/001659 dated Sep. 29, 2011, 12 pages.
Wang et al., "An Efficient Synthesis of ABT-263, A Novel Inhibitor of Antiapoptotic Bcl-2 Proteins," Synthesis, vol. 15, Jun. 11, 2008, pp. 2398-2404.
U.S. Appl. No. 61/174,274, filed Apr. 30, 2009, entitled Salt of ABT-263 and Solid-State Forms Thereof, Expired.
Extended European Search Report issued for EP 2515883 on Jun. 17, 2013, 7 pages.
International Search Report and Written Opinion received in PCT/US2010/037795 dated Dec. 21, 2010, 9 pages.
Brittain et al., Polymorphism in Pharmaceutical Solids, 1999, Chapter 1, pp. 1-10, and Chapter 5, pp. 183-226.
Byrn et al., "Pharmaceutical Solids: A Strategic Approach to Regulatory Considerations", Pharmaceutical Research, vol. 12, No. 7, pp. 945-954 (1995).

\* cited by examiner

STABILIZED LIPID FORMULATION OF APOPTOSIS PROMOTER

CROSS-REFERENCE TO RELATED APPLICATIONS

This application claims priority benefit of U.S. Provisional Application Ser. No. 61/174,299 filed on Apr. 30, 2009 and Ser. No. 61/289,254 filed on Dec. 22, 2009.

Cross-reference is made to the following co-filed U.S. applications containing subject matter related to the present application: Ser. No. 12/770,122 titled "Lipid formulation of apoptosis promoter", which claims priority benefit of U.S. provisional application Ser. No. 61/174,245 filed on Apr. 30, 2009; Ser. No. 12/770,345 titled "Salt of ABT-263 and solid-state forms thereof", which claims priority benefit of U.S. provisional application Ser. No. 61/174,274 filed on Apr. 30, 2009; and Ser. No. 12/770,299 titled "Formulation for oral administration of apoptosis promoter", which claims priority benefit of above-referenced U.S. provisional application Ser. No. 61/174,299 and Ser. No. 61/289,254, as well as Ser. No. 61/174,318 filed on Apr. 30, 2009, Ser. No. 61/185,105 filed on Jun. 8, 2009, Ser. No. 61/185,130 filed on Jun. 8, 2009, Ser. No. 61/218,281 filed on Jun. 18, 2009, and Ser. No. 61/289,289 filed on Dec. 22, 2009.

The entire disclosure of each of the above applications is incorporated herein by reference.

FIELD OF THE INVENTION

The present invention relates to pharmaceutical compositions comprising an apoptosis-promoting agent, and to methods of use thereof for treating diseases characterized by overexpression of anti-apoptotic Bcl-2 family proteins. More particularly the invention relates to such compositions exhibiting improved oral bioavailability and chemical stability of the apoptosis-promoting agent and to oral dosage regimens for administration of such a composition to a subject in need thereof.

BACKGROUND OF THE INVENTION

Evasion of apoptosis is a hallmark of cancer (Hanahan & Weinberg (2000) Cell 100:57-70). Cancer cells must overcome a continual bombardment by cellular stresses such as DNA damage, oncogene activation, aberrant cell cycle progression and harsh microenvironments that would cause normal cells to undergo apoptosis. One of the primary means by which cancer cells evade apoptosis is by up-regulation of anti-apoptotic proteins of the Bcl-2 family.

Compounds that occupy the BH3 binding groove of Bcl-2 proteins have been described, for example by Bruncko et al. (2007) *J. Med. Chem.* 50:641-662. These compounds have included N-(4-(4-((4'-chloro-(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzene-sulfonamide, otherwise known as ABT-737, which has the formula:

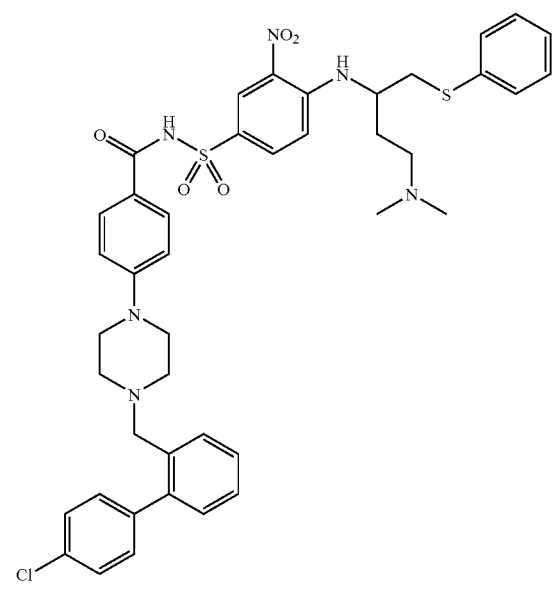 [SMILES: CN(C)CCC(CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]]

ABT-737 binds with high affinity (<1 nM) to proteins of the Bcl-2 family (specifically Bcl-2, Bcl-$X_L$ and Bcl-w). It exhibits single-agent activity against small-cell lung cancer (SCLC) and lymphoid malignancies, and potentiates pro-apoptotic effects of other chemotherapeutic agents. ABT-737 and related compounds, and methods to make such compounds, are disclosed in U.S. Patent Application Publication No. 2007/0072860 of Bruncko et al.

More recently, a further series of compounds has been identified having high binding affinity to Bcl-2 family proteins. These compounds, and methods to make them, are disclosed in U.S. Patent Application Publication No. 2007/0027135 of Bruncko et al. (herein "the '135 publication"), incorporated by reference herein in its entirety, and can be seen from their formula (Formula I below) to be structurally related to ABT-737.

In compounds of Formula I:

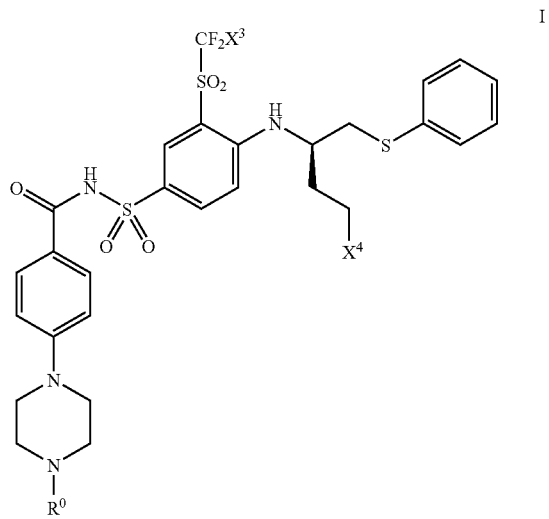

$X^3$ is chloro or fluoro; and (1) $X^4$ is azepan-1-yl, morpholin-4-yl, 1,4-oxazepan-4-yl, pyrrolidin-1-yl, $N(CH_3)_2$, $N(CH_3)(CH(CH_3)_2)$, 7-azabicyclo[2.2.1]heptan-1-yl or 2-oxa-5-azabicyclo[2.2.1]hept-5-yl; and $R^0$ is

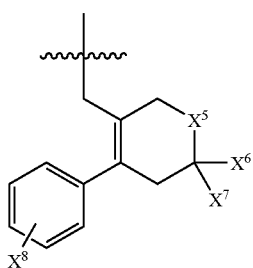

where
$X^5$ is $CH_2$, $C(CH_3)_2$ or $CH_2CH_2$;
$X^6$ and $X^7$ are both hydrogen or both methyl; and
$X^8$ is fluoro, chloro, bromo or iodo; or (2) $X^4$ is azepan-1-yl, morpholin-4-yl, pyrrolidin-1-yl, $N(CH_3)(CH(CH_3)_2)$ or 7-azabicyclo[2.2.1]heptan-1-yl; and $R^0$ is

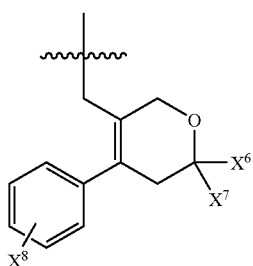

where $X^6$, $X^7$ and $X^8$ are as above; or (3) $X^4$ is morpholin-4-yl or $N(CH_3)_2$; and $R^0$ is

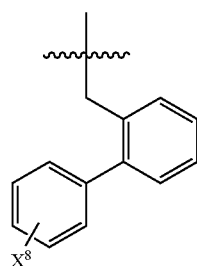

where $X^8$ is as above.

The '135 publication states that while inhibitors of Bcl-2 family proteins previously known may have either potent cellular efficacy or high systemic exposure after oral administration, they do not possess both properties. A typical measure of cellular efficacy of a compound is the concentration eliciting 50% cellular effect ($EC_{50}$). A typical measure of systemic exposure after oral administration of a compound is the area under the curve (AUC) resulting from graphing plasma concentration of the compound versus time from oral administration. Previously known compounds, it is stated in the '135 publication, have a low $AUC/EC_{50}$ ratio, meaning that they are not orally efficacious. Compounds of Formula I, by contrast, are stated to demonstrate enhanced properties with respect to cellular efficacy and systemic exposure after oral administration, resulting in a $AUC/EC_{50}$ ratio significantly higher than that of previously known compounds.

One compound, identified as "Example 1" in the '135 publication, is N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenyl sulfanyl)methyl)propyl)amino-3-((trifluoromethyl) sulfonyl) benzenesulfonamide, otherwise known as ABT-263. This compound has a molecular weight of 974.6 g/mol and has the formula:

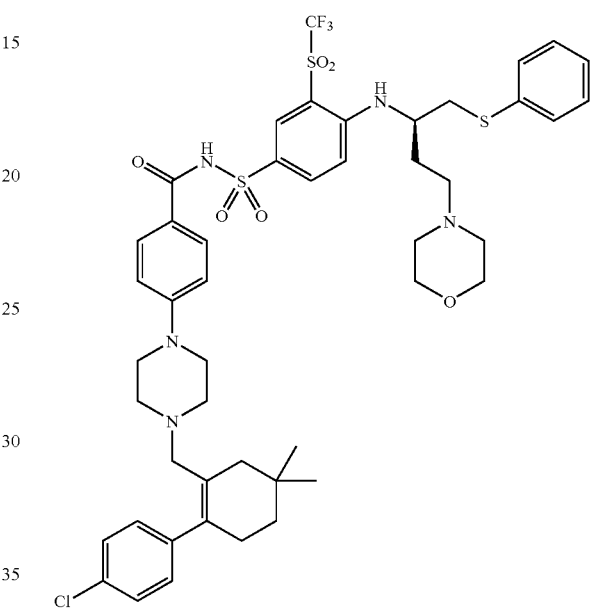

ABT-263 binds with high affinity (<1 nM) to Bcl-2 and Bcl-$X_L$ and is believed to have similarly high affinity for Bcl-w. Its $AUC/EC_{50}$ ratio is reported in the '135 publication as 56, more than an order of magnitude greater than that reported for ABT-737 (4.5). For determination of AUC according to the '135 publication, each compound was administered to rats in a single 5 mg/kg dose by oral gavage as a 2 mg/ml solution in a vehicle of 10% DMSO (dimethyl sulfoxide) in PEG-400 (polyethylene glycol of average molecular weight about 400).

Oral bioavailability (as expressed, for example, by AUC after oral administration as a percentage of AUC after intravenous administration) is not reported in the '135 publication, but can be concluded therefrom to be substantially greater for ABT-263 than for ABT-737. However, further improvement in oral bioavailability would be advantageous. Various solutions to the challenge of low oral bioavailability have been proposed in the art. For example, U.S. Pat. No. 5,645,856 to Lacy et al. proposes formulating a hydrophobic drug with (a) an oil, (b) a hydrophilic surfactant and (c) a lipophilic surfactant that substantially reduces an inhibitory effect of the hydrophilic surfactant on in vivo lipolysis of the oil, such lipolysis being said to be a factor promoting bioavailability of the drug. Among numerous classes of hydrophilic surfactants listed are phospholipids such as lecithins.

U.S. Pat. No. 6,267,985 to Chen & Patel is directed, inter alia, to a pharmaceutical composition comprising (a) a triglyceride, (b) a carrier comprising at least two surfactants, one of which is hydrophilic, and (c) a therapeutic agent capable of being solubilized in the triglyceride, the carrier or both. It is specified therein that the triglyceride and the surfactants must be present in amounts providing a clear aqueous dispersion when the composition is mixed with an aqueous solution under defined conditions. Among extensive separate lists of exemplary ingredients, mention is made of "glyceryl tricaprylate/caprate" as a triglyceride, and phospholipids including phosphatidylcholine as surfactants.

U.S. Pat. No. 6,451,339 to Patel & Chen mentions disadvantages of presence of triglycerides in such compositions, and proposes otherwise similar compositions that are substantially free of triglycerides, but that likewise provide clear aqueous dispersions.

U.S. Pat. No. 6,309,663 to Patel & Chen proposes pharmaceutical compositions comprising a combination of surfactants said to enhance bioabsorption of a hydrophilic therapeutic agent. Phospholipids such as phosphatidylcholine are again listed among exemplary surfactants.

U.S. Pat. No. 6,464,987 to Fanara et al. proposes a fluid pharmaceutical composition comprising an active substance, 3% to 55% by weight of phospholipid, 16% to 72% by weight of solvent, and 4% to 52% by weight of fatty acid. Compositions comprising Phosal 50 PG™ (primarily comprising phosphatidylcholine and propylene glycol), in some cases together with Phosal 53 MCT™ (primarily comprising phosphatidylcholine and medium chain triglycerides), are specifically exemplified. Such compositions are said to have the property of gelling instantaneously in presence of an aqueous phase and to allow controlled release of the active substance.

U.S. Pat. No. 5,538,737 to Leonard et al. proposes a capsule containing a water-in-oil emulsion wherein a water-soluble drug salt is dissolved in the water phase of the emulsion and wherein the oil phase comprises an oil and an emulsifying agent. Among oils mentioned are medium chain triglycerides; among emulsifying agents mentioned are phospholipids such as phosphatidylcholine. Phosal 53 MCT™, which contains phosphatidylcholine and medium chain triglycerides, is reportedly used according to various examples therein.

U.S. Pat. No. 5,536,729 to Waranis & Leonard proposes an oral formulation comprising rapamycin, at a concentration of about 0.1 to about 50 mg/ml, in a carrier comprising a phospholipid solution. It is stated therein that a preferred formulation can be made using Phosal 50 PG™ as the phospholipid solution. An alternative phospholipid solution mentioned is Phosal 50 MCT™.

U.S. Pat. No. 5,559,121 to Harrison et al. proposes an oral formulation comprising rapamycin, at a concentration of about 0.1 to about 100 mg/ml, in a carrier comprising N,N-dimethylacetamide and a phospholipid solution. Examples of the more preferred embodiments are shown to be prepared using Phosal 50 PG™. An alternative phospholipid solution mentioned is Phosal 50 MCT™.

U.S. Patent Application Publication No. 2007/0104780 of Lipari et al. discloses that a small-molecule drug (defined therein as having molecular weight, excluding counterions in the case of salts, not greater than about 750 g/mol, typically not greater than about 500 g/mol) having low water solubility can be formulated as a solution in a substantially non-aqueous carrier comprising at least one phospholipid and a pharmaceutically acceptable solubilizing agent. The solution, when mixed with an aqueous phase, is said to form a non-gelling, substantially non-transparent liquid dispersion. Illustratively, formulations of N-(4-(3-amino-1H-indazol-4-yl)phenyl)-N'-(2-fluoro-5-methylphenyl)urea (the protein tyrosine kinase inhibitor ABT-869) comprising Phosal 53 MCT™ and other ingredients are described therein.

Oxidation reactions represent an important degradation pathway of pharmaceuticals, especially when formulated in solution. A large body of information is available on oxidative mechanisms, but relatively few studies have been performed with specific drugs. Hovorka & Schoneich (2001) J. Pharm. Sci. 90:253-269 have stated that this lack of pharmaceutically relevant data leads to poor predictive ability with respect to drug oxidation between manufacture and administration of formulations of oxidizable drugs, and a consequently uninformed, largely empirical utilization of antioxidants in formulations.

Oxidation can occur by a number of pathways, including uncatalyzed autoxidation of a substrate by molecular oxygen, photolytic initiation, hemolytic thermal cleavage, and metal catalysis. Various functional groups show particular sensitivity towards oxidation. In particular, thioethers can degrade via hydrogen abstraction at the α-position to the sulfur atom or by addition of an α-peroxyl radical directly or via a one-electron transfer process, which transforms a sulfide to a sulfine, sulfone, or sulfoxide (Hovorka & Schöneich, supra).

The (phenylsulfanyl)methyl group of compounds of Formula I are seen to have a thioether linkage, which is susceptible to oxidation, for example in presence of oxygen or reactive oxygen species such as superoxide, hydrogen peroxide or hydroxyl radicals. The above-referenced '135 publication includes antioxidants in an extensive list of excipients said to be useful for administering a compound of Formula I.

A particular type of disease for which improved therapies are needed is non-Hodgkin's lymphoma (NHL). NHL is the sixth most prevalent type of new cancer in the U.S. and occurs primarily in patients 60-70 years of age. NHL is not a single disease but a family of related diseases, which are classified on the basis of several characteristics including clinical attributes and histology.

One method of classification places different histological subtypes into two major categories based on natural history of the disease, i.e., whether the disease is indolent or aggressive. In general, indolent subtypes grow slowly and are generally incurable, whereas aggressive subtypes grow rapidly and are potentially curable. Follicular lymphomas are the most common indolent subtype, and diffuse large-cell lymphomas constitute the most common aggressive subtype. The oncoprotein Bcl-2 was originally described in non-Hodgkin's B-cell lymphoma.

Treatment of follicular lymphoma typically consists of biologically-based or combination chemotherapy. Combination therapy with rituximab, cyclophosphamide, doxorubicin, vincristine and prednisone (R-CHOP) is routinely used, as is combination therapy with rituximab, cyclophosphamide, vincristine and prednisone (RCVP). Single-agent therapy with rituximab (targeting CD20, a phosphoprotein uniformly expressed on the surface of B-cells) or fludarabine is also used. Addition of rituximab to chemotherapy regimens can provide improved response rate and increased progression-free survival.

Radioimmunotherapy agents, high-dose chemotherapy and stem cell transplants can be used to treat refractory or relapsed non-Hodgkin's lymphoma. Currently, there is not an approved treatment regimen that produces a cure, and current guidelines recommend that patients be treated in the context of a clinical trial, even in a first-line setting.

First-line treatment of patients with aggressive large B-cell lymphoma typically consists of rituximab, cyclophosphamide, doxorubicin, vincristine and prednisone (R-CHOP), or dose-adjusted etoposide, prednisone, vincristine, cyclophosphamide, doxorubicin and rituximab (DA-EPOCH-R).

Most lymphomas respond initially to any one of these therapies, but tumors typically recur and eventually become refractory. As the number of regimens patients receive increases, the more chemotherapy-resistant the disease becomes. Average response to first-line therapy is approximately 75%, 60% to second-line, 50% to third-line, and about 35-40% to fourth-line therapy. Response rates approaching 20% with a single agent in a multiple relapsed setting are considered positive and warrant further study.

Current chemotherapeutic agents elicit their antitumor response by inducing apoptosis through a variety of mechanisms. However, many tumors ultimately become resistant to these agents. Bcl-2 and Bcl-$X_L$ have been shown to confer chemotherapy resistance in short-term survival assays in vitro and, more recently, in vivo. This suggests that if improved therapies aimed at suppressing the function of Bcl-2 and Bcl-$X_L$ can be developed, such chemotherapy-resistance could be successfully overcome.

Apoptosis-promoting drugs that target Bcl-2 family proteins such as Bcl-2 and Bcl-$X_L$ are best administered according to a regimen that provides continual, for example daily, replenishment of the plasma concentration, to maintain the concentration in a therapeutically effective range. This can be achieved by daily parenteral, e.g., intravenous (i.v.) or intraperitoneal (i.p.) administration. However, daily parenteral administration is often not practical in a clinical setting, particularly for outpatients. To enhance clinical utility of an apoptosis-promoting agent, for example as a chemotherapeutic in cancer patients, a dosage form with good oral bioavailability would be highly desirable. Such a dosage form, and a regimen for oral administration thereof, would represent an important advance in treatment of many types of cancer, including non-Hodgkin's lymphoma, and would more readily enable combination therapies with other chemotherapeutics.

It would be even more desirable to prepare such a dosage form wherein rate of oxidative degradation, particularly at the sulfur atom of the (phenylsulfanyl)methyl group of a compound of Formula I, is decreased, permitting acceptable storage stability and shelf-life of the dosage form.

SUMMARY OF THE INVENTION

It has been found that ABT-263, when formulated in solution in a lipid carrier system, exhibits substantial oxidative degradation upon storage, even under conditions where contact with atmospheric oxygen is substantially eliminated. Oxidative reactions in the case of ABT-263 include formation of a sulfoxide; the reaction providing this degradation product can be represented as follows:

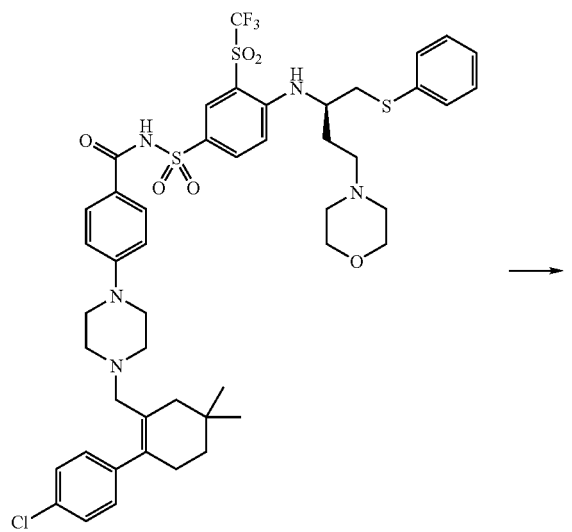

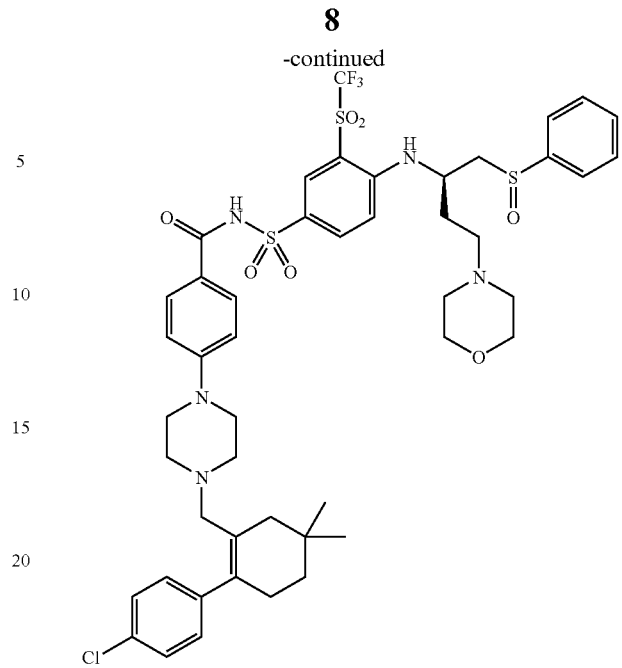

It has further been found that not all antioxidants are effective to inhibit this oxidative degradation to an acceptable degree. More particularly, it has been found that a class of antioxidants known herein as "heavier-chalcogen antioxidants" or "HCAs" exhibits superior performance in this regard by comparison with antioxidants more widely used in the art. A chalcogen is an element of Group 16 (formerly known as Group VIA) of the periodic table, including oxygen, sulfur, selenium and tellurium. A "heavier-chalcogen" herein means a chalcogen having heavier atomic weight than oxygen, specifically including sulfur and selenium. A "heavier-chalcogen antioxidant" or "HCA" is a compound having antioxidant properties that contains one or more oxidizable sulfur or selenium, most particularly sulfur, atoms.

Preparing a solution formulation of ABT-263 or a compound of Formula I together with an antioxidant-effective amount of a pharmaceutically acceptable HCA in a lipid carrier is not a simple matter of selecting a suitable HCA. A carrier system has to be selected that is capable of maintaining in solution not only the drug at a therapeutically useful concentration, but also an antioxidant-effective amount of the HCA.

There is accordingly provided an orally deliverable pharmaceutical composition comprising (a) a compound of Formula I:

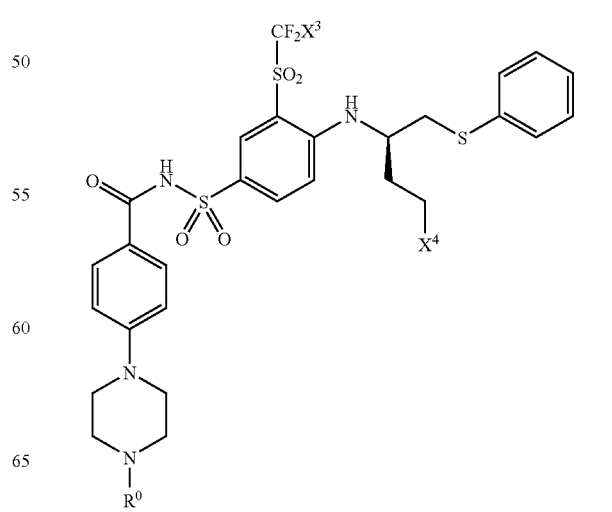

where $X^3$ is chloro or fluoro; and
(1) $X^4$ is azepan-1-yl, morpholin-4-yl, 1,4-oxazepan-4-yl, pyrrolidin-1-yl, $N(CH_3)_2$, $N(CH_3)(CH(CH_3)_2)$, 7-azabicyclo[2.2.1]heptan-1-yl or 2-oxa-5-azabicyclo[2.2.1]hept-5-yl; and $R^0$ is

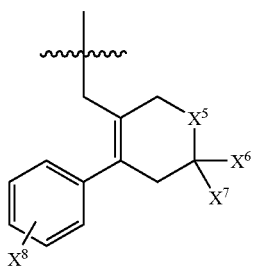

where
$X^5$ is $CH_2$, $C(CH_3)_2$ or $CH_2CH_2$;
$X^6$ and $X^7$ are both hydrogen or both methyl; and
$X^8$ is fluoro, chloro, bromo or iodo; or
(2) $X^4$ is azepan-1-yl, morpholin-4-yl, pyrrolidin-1-yl, $N(CH_3)(CH(CH_3)_2)$ or 7-azabicyclo[2.2.1]heptan-1-yl; and $R^0$ is

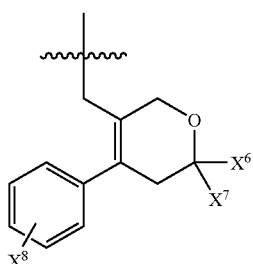

where $X^6$, $X^7$ and $X^8$ are as above; or
(3) $X^4$ is morpholin-4-yl or $N(CH_3)_2$; and $R^0$ is

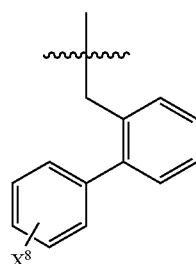

where $X^8$ is as above;
or a pharmaceutically acceptable salt, prodrug, salt of a prodrug or metabolite thereof; (b) a pharmaceutically acceptable heavier-chalcogen antioxidant; and (c) a substantially non-aqueous pharmaceutically acceptable carrier that comprises one or more lipids; wherein said compound and the antioxidant are in solution in the carrier.

There is further provided an orally deliverable pharmaceutical composition comprising (a) the compound N-(4-(4-(2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino-3-((trifluoromethyl)sulfonyl)benzenesulfonamide (ABT-263) or a salt, prodrug, salt of a prodrug or metabolite thereof; (b) a pharmaceutically acceptable heavier-chalcogen antioxidant; and (c) a substantially non-aqueous pharmaceutically acceptable carrier that comprises one or more lipids; wherein said compound and the antioxidant are in solution in the carrier. In a still more particular embodiment, the compound is ABT-263 free base or ABT-263 bis-hydrochloride salt (ABT-263 bis-HCl).

In some embodiments, the HCA is an antioxidant compound of Formula II:

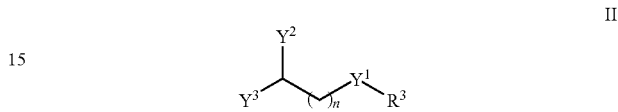

II where
n is 0, 1 or 2;
$Y^1$ is S or Se;
$Y^2$ is $NHR^1$, OH or H, where $R^1$ is alkyl or alkylcarbonyl;
$Y^3$ is $COOR^2$ or $CH_2OH$, where $R^2$ is H or alkyl; and
$R^3$ is H or alkyl;
where alkyl groups are independently optionally substituted with one of more substituents independently selected from the group consisting of carboxyl, alkylcarbonyl, alkoxycarbonyl, amino and alkylcarbonylamino; a pharmaceutically acceptable salt thereof; or, where $Y^1$ is S and $R^3$ is H, an —S—S-dimer thereof or pharmaceutically acceptable salt of such dimer.

In other embodiments, the HCA is an antioxidant compound of Formula III:

III where
Y is S, Se or S—S; and
$R^4$ and $R^5$ are independently selected from hydrogen, alkyl and $(CH_2)_nR^6$ where n is 0-10 and $R^6$ is arylcarbonyl, alkylcarbonyl, alkoxycarbonyl, carboxyl or $CHR^7R^8$-substituted alkyl, where $R^7$ and $R^8$ are independently $CO_2R^9$, $CH_2OH$, hydrogen or $NHR^{10}$, where $R^9$ is hydrogen, alkyl, substituted alkyl or arylalkyl and $R^{10}$ is hydrogen, alkyl, alkylcarbonyl or alkoxycarbonyl.

In yet other embodiments, the HCA is a poorly lipid-soluble compound, thus, as a result of introduction of the HCA as an aqueous stock solution, the carrier according to such embodiments contains water. Presence of too much water can threaten physical stability of a lipid-based solution, and can also increase rate of sulfoxide formation, negating the benefit of antioxidant addition. Typically, therefore, the carrier according to such embodiments contains no more than about 1% by weight water. (Such a carrier is still "substantially non-aqueous" as defined herein.) Suitable poorly lipid-soluble compounds include sulfites, bisulfites, metabisulfites and thiosulfates.

There is further provided a process for preparing a composition as described immediately above, comprising:
dissolving an API (active pharmaceutical ingredient) that consists essentially of the ABT-263 or salt, prodrug, salt of a prodrug or metabolite thereof in at least the phospholipid and solubilizing agent to provide a lipid solution, optionally admixing a non-phospholipid surfactant with the solubilizing agent or lipid solution, dissolving the poorly lipid-soluble antioxidant in water to prepare an aqueous stock solution, and admixing the aqueous stock solution with the lipid solution to provide an orally deliverable pharmaceutical composition.

There is still further provided a method for treating a disease characterized by apoptotic dysfunction and/or overexpression of an anti-apoptotic Bcl-2 family protein, comprising orally administering to a subject having the disease a therapeutically effective amount of a composition as described above. Examples of such a disease include many neoplastic diseases including cancers. A specific illustrative type of cancer that can be treated according to the present method is non-Hodgkin's lymphoma. Another specific illustrative type of cancer that can be treated according to the present method is chronic lymphocytic leukemia. Yet another specific illustrative type of cancer that can be treated according to the present method is acute lymphocytic leukemia, for example in a pediatric patient.

There is still further provided a method for maintaining in bloodstream of a human cancer patient, for example a patient having non-Hodgkin's lymphoma, chronic lymphocytic leukemia or acute lymphocytic leukemia, a therapeutically effective plasma concentration of ABT-263 and/or one or more metabolites thereof, comprising administering to the subject a pharmaceutical composition comprising a drug-carrier system that comprises ABT-263 or a pharmaceutically acceptable salt, prodrug, salt of a prodrug or metabolite thereof (for example ABT-263 free base or ABT-263 bis-HCl), in solution in a substantially non-aqueous carrier that comprises a pharmaceutically acceptable heavier-chalcogen antioxidant and a substantially non-aqueous pharmaceutically acceptable carrier comprising a phospholipid component and a pharmaceutically acceptable solubilizing component, wherein the ABT-263 or salt, prodrug, salt of a prodrug or metabolite thereof and the antioxidant are in solution in the carrier; in a dosage amount equivalent to about 50 to about 500 mg ABT-263 per day, at an average dosage interval of about 3 hours to about 7 days.

Additional embodiments of the invention, including more particular aspects of those provided above, will be found in, or will be evident from, the detailed description that follows.

DETAILED DESCRIPTION

Figure 1:
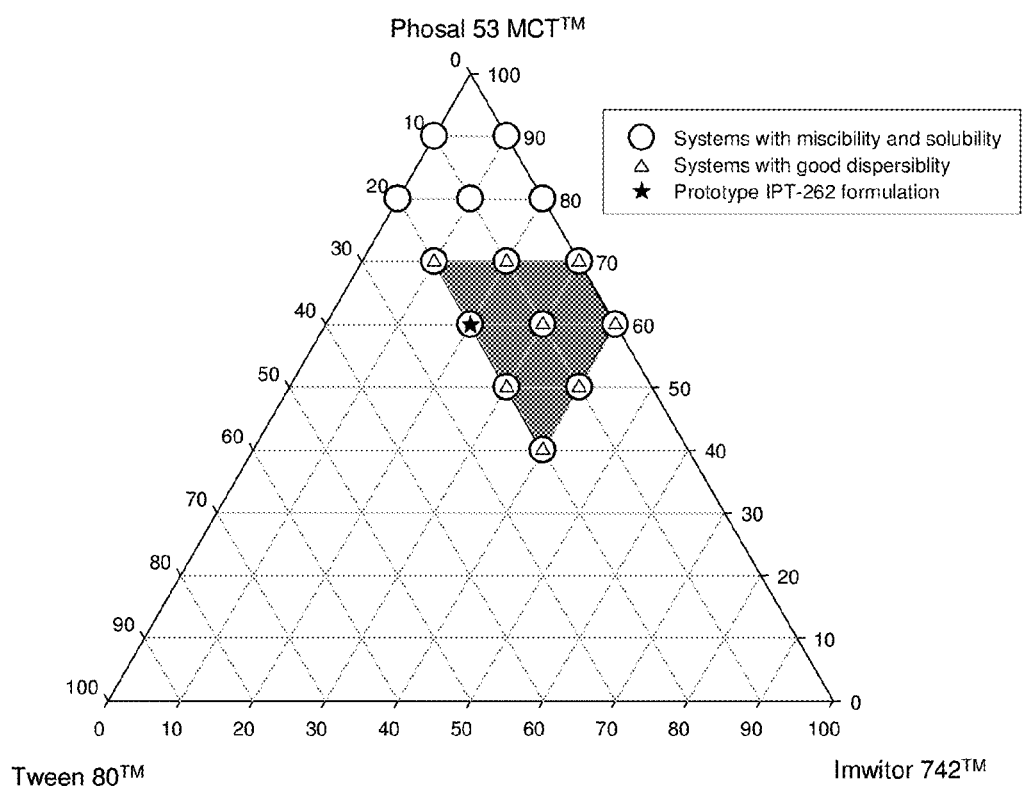
FIG. 1 is a schematic phase diagram of ABT-263 free base solutions in ternary "IPT" lipid systems as described in Example 8. The shaded portion of the diagram represents an area of optimized formulation composition.

A "drug-carrier system" herein comprises a carrier having at least one drug homogeneously distributed therein. In compositions of the present invention the drug (a compound of Formula I or a salt, prodrug, salt of a prodrug or metabolite thereof) and an antioxidant as described herein are in solution in the carrier, and, in some embodiments, the drug-carrier system constitutes essentially the entire composition. In other embodiments, the drug-carrier system is encapsulated within a capsule shell that is suitable for oral administration; in such embodiments the composition comprises the drug-carrier system and the capsule shell.

The carrier and the drug-carrier system are typically liquid, but in some embodiments the carrier and/or the drug-carrier system can be solid or semi-solid. For example, a drug-carrier system can illustratively be prepared by dissolving the drug and antioxidant in a carrier at a temperature above the melting or flow point of the carrier, and cooling the resulting solution to a temperature below the melting or flow point to provide a solid drug-carrier system. Alternatively or in addition, the carrier can comprise a solid substrate wherein or whereon a solution of the drug and antioxidant as described herein is adsorbed.

A composition of the invention is "orally deliverable", i.e., adapted for oral administration; however, such a composition can be useful for delivery of the drug to a subject in need thereof by other routes of administration, including without limitation parenteral, sublingual, buccal, intranasal, pulmonary, topical, transdermal, intradermal, ocular, otic, rectal, vaginal, intragastric, intracranial, intrasynovial and intra-articular routes.

The terms "oral administration" and "orally administered" herein refer to administration to a subject per os (p.o.), that is, administration wherein the composition is immediately swallowed, for example with the aid of a suitable volume of water or other potable liquid. "Oral administration" is distinguished herein from intraoral administration, e.g., sublingual or buccal administration or topical administration to intraoral tissues such as periodontal tissues, that does not involve immediate swallowing of the composition.

Therapeutically active compounds, including salts, prodrugs, salts of prodrugs and metabolites thereof, useful herein typically have low solubility in water, for example less than about 100 µg/ml, in most cases less than about 30 µg/ml. The present invention can be especially advantageous for drugs that are essentially insoluble in water, i.e., having a solubility of less than about 10 µg/ml. It will be recognized that aqueous solubility of many compounds is pH dependent; in the case of such compounds the solubility of interest herein is at a physiologically relevant pH, for example a pH of about 1 to about 8. Thus, in various embodiments, the drug has a solubility in water, at least at one point in a pH range from about 1 to about 8, of less than about 100 µg/ml, for example less than about 30 µg/ml, or less than about 10 µg/ml. Illustratively, ABT-263 has a solubility in water at pH 2 of less than 4 µg/ml.

In one embodiment, the composition comprises a compound of Formula I as defined above, or a pharmaceutically acceptable salt, prodrug, salt of a prodrug or metabolite of such a compound.

In a further embodiment, the compound has Formula I where $X^3$ is fluoro.

In a still further embodiment, the compound has Formula I where $X^4$ is morpholin-4-yl.

In a still further embodiment, the compound has Formula I where $R^0$ is

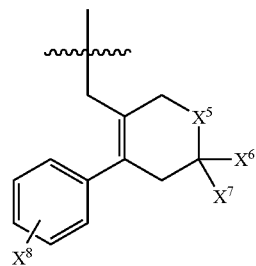

where $X^5$ is O, $CH_2$, $C(CH_3)_2$ or $CH_2CH_2$; $X^6$ and $X^7$ are both hydrogen or both methyl; and $X^8$ is fluoro, chloro, bromo or iodo. Illustratively according to this embodiment $X^5$ can be $CH_2$ or $C(CH_3)_2$ and/or each of $X^6$ and $X^7$ can be methyl and/or $X^8$ can be chloro.

In a still further embodiment, the compound has Formula I where $R^0$ is

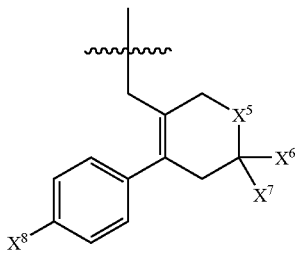

where $X^5$ is O, $CH_2$, $C(CH_3)_2$ or $CH_2CH_2$; $X^6$ and $X^7$ are both hydrogen or both methyl; and $X^8$ is fluoro, chloro, bromo or iodo. Illustratively according to this embodiment $X^5$ can be $CH_2$ or $C(CH_3)_2$ and/or each of $X^6$ and $X^7$ can be methyl and/or $X^8$ can be chloro.

In a still further embodiment, the compound has Formula I where $X^3$ is fluoro and $X^4$ is morpholin-4-yl.

In a still further embodiment, the compound has Formula I where $X^3$ is fluoro and $R^0$ is

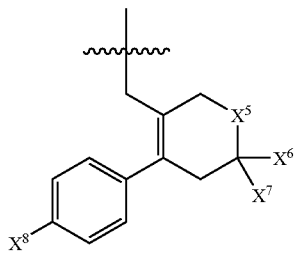

where $X^5$ is O, $CH_2$, $C(CH_3)_2$ or $CH_2CH_2$; $X^6$ and $X^7$ are both hydrogen or both methyl; and $X^8$ is fluoro, chloro, bromo or iodo. Illustratively according to this embodiment $X^5$ can be $CH_2$ or $C(CH_3)_2$ and/or each of $X^6$ and $X^7$ can be methyl and/or $X^8$ can be chloro.

In a still further embodiment, the compound has Formula I where $X^4$ is morpholin-4-yl and $R^0$ is

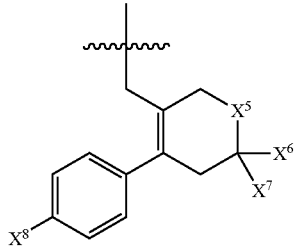

where $X^5$ is O, $CH_2$, $C(CH_3)_2$ or $CH_2CH_2$; $X^6$ and $X^7$ are both hydrogen or both methyl; and $X^8$ is fluoro, chloro, bromo or iodo. Illustratively according to this embodiment $X^5$ can be $CH_2$ or $C(CH_3)_2$ and/or each of $X^6$ and $X^7$ can be methyl and/or $X^8$ can be chloro.

In a still further embodiment, the compound has Formula I where $X^3$ is fluoro, $X^4$ is morpholin-4-yl and $R^0$ is

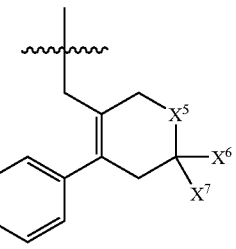

where $X^5$ is O, $CH_2$, $C(CH_3)_2$ or $CH_2CH_2$; $X^6$ and $X^7$ are both hydrogen or both methyl; and $X^8$ is fluoro, chloro, bromo or iodo. Illustratively according to this embodiment $X^5$ can be $CH_2$ or $C(CH_3)_2$ and/or each of $X^6$ and $X^7$ can be methyl and/or $X^8$ can be chloro.

Compounds of Formula I may contain asymmetrically substituted carbon atoms in the R- or S-configuration; such compounds can be present as racemates or in an excess of one configuration over the other, for example in an enantiomeric ratio of at least about 85:15. The compound can be substantially enantiomerically pure, for example having an enantiomeric ratio of at least about 95:5, or in some cases at least about 98:2 or at least about 99:1.

Compounds of Formula I may alternatively or additionally contain carbon-carbon double bonds or carbon-nitrogen double bonds in the Z- or E-configuration, the term "Z" denoting a configuration wherein the larger substituents are on the same side of such a double bond and the term "E" denoting a configuration wherein the larger substituents are on opposite sides of the double bond. The compound can alternatively be present as a mixture of Z- and E-isomers.

Compounds of Formula I may alternatively or additionally exist as tautomers or equilibrium mixtures thereof wherein a proton shifts from one atom to another. Examples of tautomers illustratively include keto-enol, phenol-keto, oxime-nitroso, nitro-aci, imine-enamine and the like.

In some embodiments, a compound of Formula I is present in the composition in its parent-compound form, alone or together with a salt or prodrug form of the compound.

Compounds of Formula I may form acid addition salts, basic addition salts or zwitterions. Salts of compounds of Formula I can be prepared during isolation or following purification of the compounds. Acid addition salts are those derived from reaction of a compound of Formula I with an acid. For example, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate and undecanoate salts of a compound of Formula I can be used in a composition of the invention. Basic addition salts including those derived from reaction of a compound with the bicarbonate, carbonate, hydroxide or phosphate of cations such as lithium, sodium, potassium, calcium and magnesium can likewise be used.

A compound of Formula I typically has more than one protonatable nitrogen atom and is consequently capable of forming acid addition salts with more than one, for example about 1.2 to about 2, about 1.5 to about 2 or about 1.8 to about 2, equivalents of acid per equivalent of the compound.

ABT-263 can likewise form acid addition salts, basic addition salts or zwitterions. Salts of ABT-263 can be prepared during isolation or following purification of the compound. Acid addition salts derived from reaction of ABT-263 with an acid include those listed above. Basic addition salts including those listed above can likewise be used. ABT-263 has at least two protonatable nitrogen atoms and is consequently capable of forming acid addition salts with more than one, for example about 1.2 to about 2, about 1.5 to about 2 or about 1.8 to about 2, equivalents of acid per equivalent of the compound.

Illustratively in the case of ABT-263, bis-salts can be formed including, for example, bis-hydrochloride (bis-HCl) and bis-hydrobromide (bis-HBr) salts.

For example, ABT-263 bis-HCl, which has a molecular weight of 1047.5 g/mol and is represented by the formula

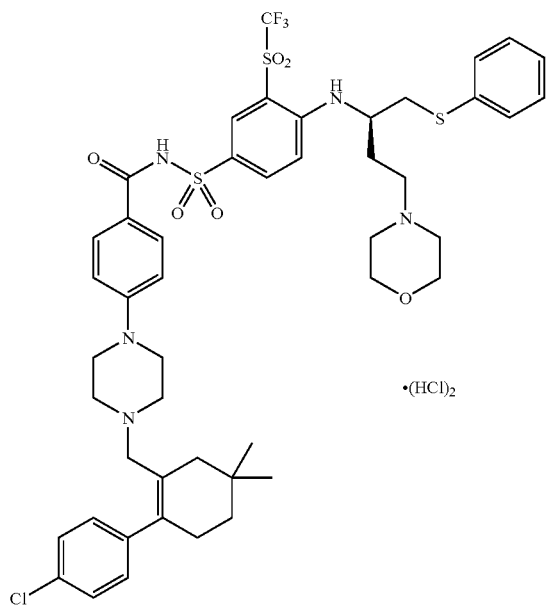

can be prepared by a variety of processes, for example a process that can be outlined as follows.

ABT-263 free base is prepared, illustratively as described in Example 1 of the above-cited '135 publication, the entire disclosure of which is incorporated by reference herein. A suitable weight of ABT-263 free base is dissolved in ethyl acetate. A solution of hydrochloric acid in ethanol (for example about 4.3 kg HCl in 80 g EtOH) is added to the ABT-263 solution in an amount providing at least 2 mol HCl per mol ABT-263 and sufficient EtOH (at least about 20 vol) for crystallization of the resulting ABT-263 bis-HCl salt. The solution is heated to about 45° C. with stirring and seeds are added as a slurry in EtOH. After about 6 hours, the resulting slurry is cooled to about 20° C. over about 1 hour and is mixed at that temperature for about 36 hours. The slurry is filtered to recover a crystalline solid, which is an ethanol solvate of ABT-263 bis-HCl. Drying of this solid under vacuum and nitrogen with mild agitation for about 8 days yields white desolvated ABT-263 bis-HCl crystals. This material is suitable for preparation of an ABT-263 bis-HCl formulation of the present invention.

The term "free base" is used for convenience herein to refer to the parent compound, while recognizing that the parent compound is, strictly speaking, zwitterionic and thus does not always behave as a true base.

As indicated above, ABT-263 free base can be prepared by a process as described in Example 1 of the above-cited '135 publication. The product of this process is an amorphous, glassy solid. A powder can be prepared from this product, for example by freeze-drying or precipitation techniques. Such a powder can be used as API in preparing a capsule of the present invention; however, it will generally be found preferable to use a crystalline form of ABT-263 free base as API. Such crystalline forms include solvates and solvent-free crystalline forms.

Solvates of ABT-263 free base can be prepared as described below. The starting product can be any solid-state form of ABT-263 free base, including the amorphous form prepared according to the '135 publication.

A measured amount of ABT-263 free base (as indicated, any solid-state form can be used) is suspended in any of a number of solvents or solvent mixtures, including without limitation 2-propanol, 1-propanol, ethyl acetate/ethanol 1:3 v/v, methyl acetate/hexanes 1:1 v/v, chloroform, methanol, 1,4-dioxane/hexanes 1:2 v/v, toluene and benzene. The resulting suspension is agitated at ambient temperature, while protected from light. After a period of time sufficient to permit solvation of ABT-263 free base in each case, crystals are harvested by filter centrifugation. The resulting solvates can be characterized by powder X-ray diffraction (PXRD), for example using a G3000 diffractometer (Inel Corp., Artenay, France) equipped with a curved position-sensitive detector and parallel-beam optics. The diffractometer is operated with a copper anode tube (1.5 kW fine focus) at 40 kV and 30 mA. An incident-beam germanium monochromator provides monochromatic radiation. The diffractometer is calibrated using an attenuated direct beam at one-degree intervals. Calibration is checked using a silicon powder line position reference standard (NIST 640c). The instrument is computer-controlled using Symphonix software (Inel Corp., Artenay, France) and the data are analyzed using Jade software (version 6.5, Materials Data, Inc., Livermore, Calif.). The sample is loaded onto an aluminum sample holder and leveled with a glass slide.

Desolvation of an ethyl acetate/ethanol solvate, for example by air-drying, provides a solvent-free crystalline form of ABT-263 free base. PXRD peaks for Form I ABT-263 free base are listed in Table 1. A PXRD pattern having peaks substantially as indicated therein can be used to identify crystalline ABT-263 free base, more particularly Form I ABT-263 free base. The phrase "substantially as indicated" in the present context means having peaks that are not shifted more than about 0.2° 2θ from the indicated position.

TABLE 1

| PXRD peak listing: solvent-free crystal polymorph Form I ABT-263 free base Peak Position (° 2θ) |
| --- |
| 6.21 |
| 6.72 |
| 9.66 |
| 10.92 |
| 11.34 |
| 12.17 |
| 14.28 |
| 16.40 |
| 16.95 |
| 17.81 |

TABLE 1-continued

PXRD peak listing: solvent-free crystal polymorph
Form I ABT-263 free base
Peak Position (° 2θ)

18.03
18.47
19.32
20.10
21.87

Desolvation of most solvates, including 1-propanol, 2-propanol, methanol, benzene, toluene, dioxane/hexanes, methyl acetate/hexanes and chloroform solvates, provides a solvent-free crystalline form of ABT-263 free base that is shown by PXRD to be identical to the crystalline form produced by desolvation of the ethyl acetate/ethanol solvate.

Figure 2:
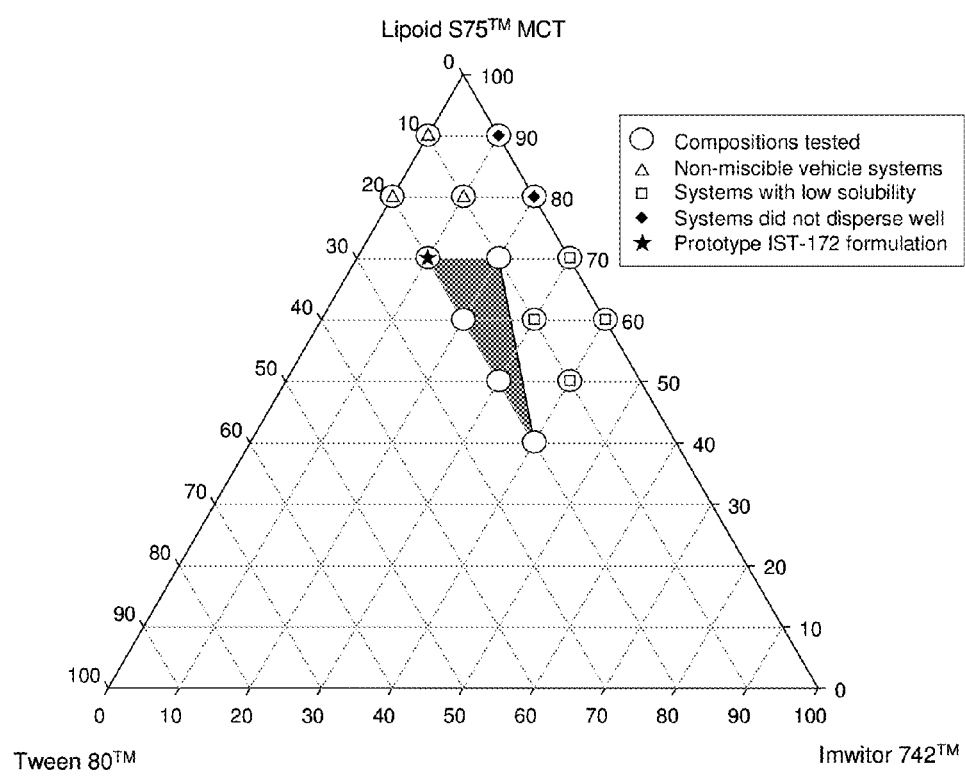
FIG. 2 is a schematic phase diagram of ABT-263 free base solutions in ternary "IST" lipid systems as described in Example 8. The shaded portion of the diagram represents an area of optimized formulation composition.

Desolvation of pyridine and anisole solvates provides a solvent-free crystalline form of ABT-263 free base that is shown by PXRD to be different from the form produced by desolvation of the ethyl acetate/ethanol solvate. The crystalline form derived from desolvation of the pyridine or anisole solvate is designated Form II. A PXRD scan of Form II ABT-263 free base is shown in FIG. 2. PXRD peaks for Form II ABT-263 free base are listed in Table 2. A PXRD pattern having peaks substantially as indicated therein can be used to identify crystalline ABT-263 free base, more particularly Form II ABT-263 free base.

TABLE 2

PXRD peak listing: solvent-free crystal polymorph
Form II ABT-263 free base
Peak Position (° 2θ)

5.79
8.60
9.34
10.79
11.36
11.59
12.76
13.23
13.73
14.01
14.72
15.00
16.28
17.07
17.48
18.75
19.34
19.71
20.56
21.35

PXRD peaks especially diagnostic for Form I ABT-263 free base, in particular for distinguishing Form I from Form II, include the peaks at 6.21, 6.72, 12.17, 18.03 and 20.10° 2θ, in each case±0.2° 2θ. In one embodiment, Form I ABT-263 free base is characterized at least by a peak at any one or more of these positions. In another embodiment, Form I ABT-263 free base is characterized at least by a peak at each of these positions. In yet another embodiment, Form I ABT-263 free base is characterized by a peak at each of the positions shown in Table 1.

PXRD peaks especially diagnostic for Form II ABT-263 free base, in particular for distinguishing Form II from Form I, include the peaks at 5.79, 8.60, 12.76, 15.00 and 2θ, in each case±0.2° 2θ. In one embodiment, Form II ABT-263 free base is characterized at least by a peak at any one or more of these positions. In another embodiment, Form II ABT-263 free base is characterized at least by a peak at each of these positions. In yet another embodiment, Form II ABT-263 free base is characterized by a peak at each of the positions shown in Table 2.

Any of the crystalline forms of ABT-263 free base, including solvated forms, can be useful as API for preparation of a capsule of the present invention. However, solvent-free forms such as Form I and Form II are generally preferred for this purpose.

Compounds of Formula I, and methods of preparation of such compounds, are disclosed in the above-cited '135 publication and/or in above-cited U.S. Patent Application Publication No. 2007/0072860, each of which is incorporated herein by reference in its entirety. Terms for substituents used herein are defined exactly as in those publications.

Compounds of Formula I having —NH, —C(O)OH, —OH or —SH moieties may have attached thereto prodrug-forming moieties which can be removed by metabolic processes in vivo to release the parent compound having free —NH, —C(O)OH, —OH or —SH moieties. Salts of prodrugs can also be used.

Without being bound by theory, it is believed that the therapeutic efficacy of compounds of Formula I is due at least in part to their ability to bind to a Bcl-2 family protein such as Bcl-2, Bcl-$X_L$ or Bcl-w in a way that inhibits the anti-apoptotic action of the protein, for example by occupying the BH3 binding groove of the protein. It will generally be found desirable to select a compound having high binding affinity for a Bcl-2 family protein, for example a $K_i$ not greater than about 5 nM, preferably not greater than about 1 nM.

A composition as provided herein comprising any specific compound disclosed in the '135 publication is expressly contemplated as an embodiment of the present invention.

In a more particular embodiment, the composition comprises N-(4-(4-((2-(4-chlorophenyl)-5,5-dimethyl-1-cyclohex-1-en-1-yl)methyl)piperazin-1-yl)benzoyl)-4-(1R)-3-(morpholin-4-yl)-1-((phenyl sulfanyl)methyl)propyl)amino-3-((trifluoromethyl) sulfonyl)benzenesulfonamide (ABT-263) or a salt, prodrug, salt of a prodrug or metabolite thereof. In a still more particular embodiment, the composition comprises ABT-263 parent compound (i.e., free base) or a salt, prodrug or salt of a prodrug thereof. In a still more particular embodiment, the composition comprises ABT-263 free base or a salt, for example a bis-salt, thereof. In an even more particular embodiment, the composition comprises ABT-263 free base or ABT-263 bis-HCl.

The drug (i.e., a compound of Formula I or a salt, prodrug, salt of a prodrug or metabolite thereof) is present in the composition in an amount that can be therapeutically effective when the composition is administered to a subject in need thereof according to an appropriate regimen. Dosage amounts are expressed herein as parent-compound-equivalent amounts unless the context requires otherwise. Typically, a unit dose (the amount administered at a single time), which can be administered at an appropriate frequency, e.g., twice daily to once weekly, is about 10 to about 1,000 mg, depending on the compound in question. Where frequency of administration is once daily (q.d.), unit dose and daily dose are the same. Illustratively, for example where the drug is ABT-263, the unit dose is typically about 25 to about 1,000 mg, more typically about 50 to about 500 mg, for example about 50, about 100, about 150, about 200, about 250, about 300, about 350, about 400, about 450 or about 500 mg. Where the composition comprises a capsule shell enclosing the drug-carrier system, a unit dose can be deliverable in a single capsule or a small plurality of capsules, most typically 1 to about 10 capsules.

The higher the unit dose, the more desirable it becomes to select a carrier that permits a relatively high concentration of the drug in solution therein. Typically, the concentration of drug in the drug-carrier system is at least about 10 mg/ml, e.g., about 10 to about 500 mg/ml, but lower and higher concentrations can be acceptable or achievable in specific cases. Illustratively, for example where the drug is ABT-263, the drug concentration in various embodiments is at least about 10 mg/ml, e.g., about 10 to about 400 mg/ml, or at least about 20 mg/ml, e.g., about 20 to about 200 mg/ml, for example about 20, about 25, about 30, about 40, about 50, about 75, about 100, about 125, about 150 or about 200 mg/ml.

In a composition of the invention, the drug is "in solution" in the carrier. This will be understood to mean that substantially all of the drug is in solution, i.e., no substantial portion, for example no more than about 2%, or no more than about 1%, of the drug is in solid (e.g., crystalline) form, whether dispersed, for example in the form of a suspension, or not. In practical terms, this means that the drug must normally be formulated at a concentration below its limit of solubility in the carrier. It will be understood that the limit of solubility can be temperature-dependent, thus selection of a suitable concentration should take into account the range of temperatures to which the composition is likely to be exposed in normal storage, transport and use.

Not only the drug, but also the antioxidant, is "in solution" as defined above in the carrier. Where the antioxidant is poorly lipid-soluble and has to be introduced to the carrier or drug-carrier system in aqueous solution, a surfactant, more particularly a non-phospholipid surfactant, may be necessary to avoid phase separation.

An "antioxidant" or compound having "antioxidant" properties is a chemical compound that prevents, inhibits, reduces or retards oxidation of another chemical or itself. Antioxidants can improve stability and shelf-life of a lipid formulation as described herein by, for example, preventing, inhibiting, reducing or retarding oxidation of the compound of Formula I in the formulation.

Enhancement of stability or shelf-life can be evaluated, for example, by monitoring rate of appearance or build-up of sulfoxides in the formulation. Sulfoxides in total can be monitored by repeated sampling and analysis; alternatively samples can be analyzed more specifically for the sulfoxide degradation product of the compound of Formula I, i.e., the compound having the formula

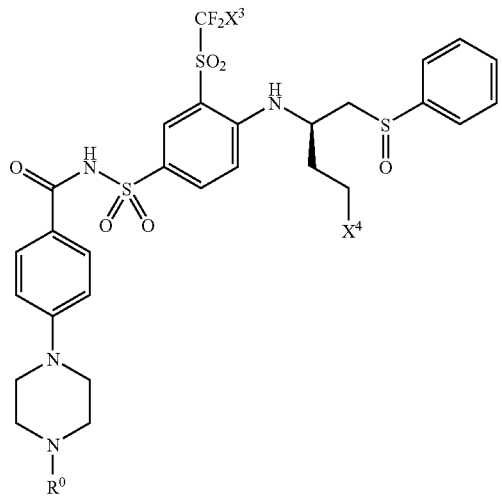

where $X^3$, $X^4$ and $R^0$ are as indicated above; or the sulfoxide degradation product of ABT-263, having the formula

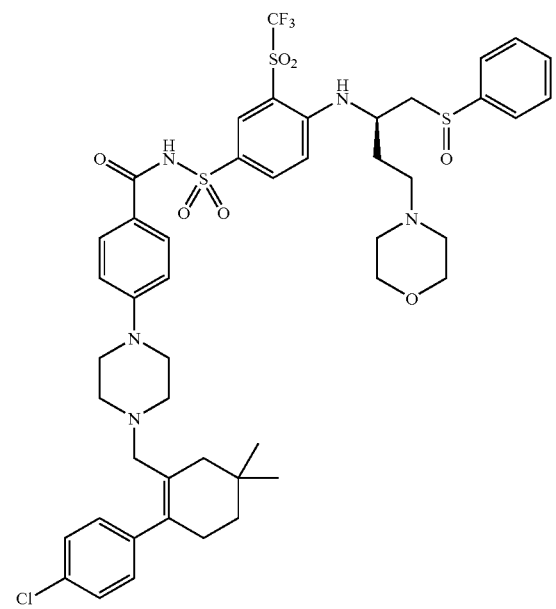

Reference herein to the sulfoxide degradation product will be understood to include both diastereomers at the sulfur atom stereocenter in the sulfoxide group.

An "antioxidant effective amount" of an antioxidant herein is an amount that provides (a) a substantial reduction (for example a reduction of at least about 25%, at least about 50%, at least about 75%, at least about 80%, at least about 85% or at least about 90%) in the formation or accumulation of a degradation product, for example the sulfoxide degradation product above, and/or (b) a substantial increase (for example at least about 30, at least about 60, at least about 90 or at least about 180 days) in the time taken for the degradation product to reach a threshold level, in a formulation containing the antioxidant, by comparison with an otherwise similar formulation containing no antioxidant. A storage-stability study to determine degree of (a) reduction in formation or accumulation of the degradation product or (b) increase in time taken for a degradation product to reach a threshold level in the formulation can be conducted at any appropriate temperature or range of temperatures. Illustratively, a study at about 5° C. can be indicative of storage stability under refrigerated conditions, a study at about 20-25° C. can be indicative of storage stability under typical ambient conditions, and a study at about 30° C. or higher temperature can be useful in an accelerated-aging study. Any appropriate threshold level of the degradation product can be selected as an end-point, for example in the range from about 0.2% to about 2% of the initial amount of the compound of Formula I present.

In various illustrative embodiments, the antioxidant is included in an amount effective to hold oxidative degradation of the drug (a) below about 1% for at least about 3 months;
(b) below about 1% for at least about 6 months;
(c) below about 1% for at least about 1 year;
(d) below about 0.5% for at least about 3 months;
(e) below about 0.5% for at least about 6 months; or
(f) below about 0.5% for at least about 1 year;

in the formulation when stored under ambient conditions (e.g., about 20-25° C.) in a sealed container opaque to ultraviolet light, as measured for example by amount of the sulfoxide degradation product present at the end of the recited storage period.

Antioxidants used in pharmaceutical compositions are most typically agents that inhibit generation of oxidative species such as triplet or singlet oxygen, superoxides, peroxide and free hydroxyl radicals, or agents that scavenge such oxidative species as they are generated. Examples of commonly used antioxidants of these classes include butylated hydroxyanisole (BHA), butylated hydroxytoluene (BHT), retinyl palmitate, tocopherol, propyl gallate, ascorbic acid and ascorbyl palmitate. The present inventors have found, however, that at least some commonly used antioxidants are ineffective to protect ABT-263 from excessive sulfoxide formation in encapsulated liquid formulations as described herein.

For example, BHA, added at 0.2% by weight to a 15% by weight solution of ABT-263 free base in a medium referred to herein as "IPT-253" (20% Imwitor 742™, 50% Phosal 53 MCT™, 30% Tween™ 80), has been found to have no effect on sulfoxide formation in a 4-week stability study at 40° C. without nitrogen purging of headspace, as shown in Table 3. A full report of this study is found in Example 7 herein.

TABLE 3

Effect of 0.2% BHA on ABT-263 sulfoxide formation in IPT-253 solution

| Time | % Total sulfoxides | |
|---|---|---|
| (weeks) | No antioxidant | 0.2% BHA |
| 0 | not detectable | 0.06 |
| 1 | 0.26 | 0.29 |
| 2 | 0.47 | 0.49 |
| 3 | 0.56 | 0.58 |
| 4 | 0.67 | 0.68 |

Antioxidants that, by contrast, have been found effective are heavier-chalcogen antioxidants that are believed, without being bound by theory, to function primarily as competitive substrates, i.e., as "sacrificial" antioxidants, which are preferentially attacked by oxidative species thereby protecting the drug from excessive degradation.

In some embodiments, the HCA comprises one or more antioxidant compounds of Formula II:

$$Y^3 \overset{Y^2}{\underset{(\ )_n}{\diagup}} \overset{Y^1}{\diagdown} R^3 \quad \text{II}$$

where
  n is 0, 1 or 2;
  $Y^1$ is S or Se;
  $Y^2$ is $NHR^1$, OH or H, where $R^1$ is alkyl or alkylcarbonyl;
  $Y^3$ is $COOR^2$ or $CH_2OH$, where $R^2$ is H or alkyl; and
  $R^3$ is H or alkyl;
where alkyl groups are independently optionally substituted with one of more substituents independently selected from the group consisting of carboxyl, alkylcarbonyl, alkoxycarbonyl, amino and alkylcarbonylamino; a pharmaceutically acceptable salt thereof; or, where $Y^1$ is S and $R^3$ is H, an —S—S— dimer thereof or pharmaceutically acceptable salt of such dimer.

In other embodiments, the HCA is an antioxidant compound of Formula III:

$$R^4 \overset{Y}{\diagdown} R^5 \quad \text{III}$$

where
  Y is S, Se or S—S; and
  $R^4$ and $R^5$ are independently selected from H, alkyl and $(CH_2)_n R^6$ where n is 0-10 and $R^6$ is arylcarbonyl, alkylcarbonyl, alkoxycarbonyl, carboxyl or $CHR^7 R^8$-substituted alkyl, where $R^7$ and $R^8$ are independently $CO_2 R^9$, $CH_2OH$, hydrogen or $NHR^{10}$, where $R^9$ is H, alkyl, substituted alkyl or arylalkyl and $R^{10}$ is hydrogen, alkyl, alkylcarbonyl or alkoxycarbonyl.

An "alkyl" substituent or an "alkyl" or "alkoxy" group forming part of a substituent according to Formula II or Formula III is one having 1 to about 18 carbon atoms and can consist of a straight or branched chain.

An "aryl" group forming part of a substituent according to Formula III is a phenyl group, unsubstituted or substituted with one or more hydroxy, alkoxy or alkyl groups.

In some embodiments, $R^2$ in Formula II is $C_{1-4}$ alkyl (e.g., methyl or ethyl) or ($C_{1-4}$ alkyl)carbonyl (e.g., acetyl).

In some embodiments, $R^2$ in Formula II is H or $C_{1-18}$ alkyl, for example methyl, ethyl, propyl (e.g., n-propyl or isopropyl), butyl (e.g., n-butyl, isobutyl or t-butyl), octyl (e.g., n-octyl or 2-ethylhexyl), dodecyl (e.g., lauryl), tridecyl, tetradecyl, hexadecyl or octadecyl (e.g., stearyl).

$R^3$ is typically H or $C_{1-4}$ alkyl (e.g., methyl or ethyl).

The HCA can be, for example, a natural or synthetic amino acid or a derivative thereof such as an alkyl ester or N-acyl derivative, or a salt of such amino acid or derivative. Where the amino acid or derivative thereof is derived from a natural source it is typically in the L-configuration; however it is understood that D-isomers and D,L-isomer mixtures can be substituted if necessary.

Non-limiting examples of HCAs useful herein include β-alkylmercaptoketones, cysteine, cystine, homocysteine, methionine, thiodiglycolic acid, thiodipropionic acid, thioglycerol, selenocysteine, selenomethionine and salts, esters, amides and thioethers thereof; and combinations thereof. More particularly, one or more HCAs can be selected from N-acetylcysteine, N-acetylcysteine butyl ester, N-acetylcysteine dodecyl ester, N-acetylcysteine ethyl ester, N-acetylcysteine methyl ester, N-acetylcysteine octyl ester, N-acetylcysteine propyl ester, N-acetylcysteine stearyl ester, N-acetylcysteine tetradecyl ester, N-acetylcysteine tridecyl ester, N-acetylmethionine, N-acetylmethionine butyl ester, N-acetylmethionine dodecyl ester, N-acetylmethionine ethyl ester, N-acetylmethionine methyl ester, N-acetylmethionine octyl ester, N-acetylmethionine propyl ester, N-acetylmethionine stearyl ester, N-acetylmethionine tetradecyl ester, N-acetylmethionine tridecyl ester, N-acetylselenocysteine, N-acetylselenocysteine butyl ester, N-acetylselenocysteine dodecyl ester, N-acetylselenocysteine ethyl ester, N-acetylselenocysteine methyl ester, N-acetylseleno-cysteine octyl ester, N-acetylselenocysteine propyl ester, N-acetylselenocysteine stearyl ester, N-acetylselenocysteine tetradecyl ester, N-acetylselenocysteine tridecyl ester, N-acetylselenomethionine, N-acetylselenomethionine butyl ester, N-acetylselenomethionine dodecyl ester, N-acetylselenomethionine ethyl ester, N-acetylselenomethionine methyl ester, N-acetyl-selenomethionine octyl ester, N-acetylselenomethionine propyl ester, N-acetylselenomethionine stearyl ester, N-acetylselenomethionine tetradecyl ester, N-acetylselenomethionine tridecyl ester, cysteine, cysteine butyl ester, cysteine dodecyl ester, cysteine ethyl ester, cysteine methyl ester, cysteine octyl ester, cysteine propyl ester, cysteine stearyl ester, cysteine tetradecyl ester, cysteine tridecyl ester, cystine, cystine dibutyl ester, cystine di(dodecyl) ester, cystine diethyl ester, cystine dimethyl ester, cystine dioctyl ester, cystine dipropyl ester, cystine distearyl ester, cystine di(tetradecyl) ester, cystine di(tridecyl) ester, N,N-diacetylcystine, N,N-diacetylcystine dibutyl ester, N,N-diacetylcystine diethyl ester, N,N-diacetylcystine di(dodecyl) ester, N,N-diacetylcystine dimethyl ester, N,N-diacetylcystine dioctyl ester, N,N-diacetylcystine dipropyl ester, N,N-diacetylcystine distearyl ester, N,N-diacetylcystine di(tetradecyl) ester, N,N-diacetylcystine di(tridecyl) ester, dibutyl thiodiglycolate, dibutyl thiodipropionate, di(dodecyl) thiodiglycolate, di(dodecyl) thiodipropionate, diethyl thiodiglycolate, diethyl thiodipropionate, dimethyl thiodiglycolate, dimethyl thiodipropionate, dioctyl thiodiglycolate, dioctyl thiodipropionate, dipropyl thiodiglycolate, dipropyl thiodipropionate, distearyl thiodiglycolate, distearyl thiodipropionate, di(tetradecyl) thiodiglycolate, di(tetradecyl) thiodipropionate, homocysteine, homocysteine butyl ester, homocysteine dodecyl ester, homocysteine ethyl ester, homocysteine methyl ester, homocysteine octyl ester, homocysteine propyl ester, homocysteine stearyl ester, homocysteine tetradecyl ester, homocysteine tridecyl ester, methionine, methionine butyl ester, methionine dodecyl ester, methionine ethyl ester, methionine methyl ester, methionine octyl ester, methionine propyl ester, methionine stearyl ester, methionine tetradecyl ester, methionine tridecyl ester, S-methylcysteine, S-methylcysteine butyl ester, S-methylcysteine dodecyl ester, S-methylcysteine ethyl ester, S-methylcysteine methyl ester, S-methylcysteine octyl ester, S-methylcysteine propyl ester, S-methylcysteine stearyl ester, S-methylcysteine tetradecyl ester, S-methylcysteine tridecyl ester, selenocysteine, selenocysteine butyl ester, selenocysteine dodecyl ester, selenocysteine ethyl ester, selenocysteine methyl ester, selenocysteine octyl ester, selenocysteine propyl ester, selenocysteine stearyl ester, selenocysteine tetradecyl ester, selenocysteine tridecyl ester, selenomethionine, selenomethionine butyl ester, selenomethionine dodecyl ester, selenomethionine ethyl ester, selenomethionine methyl ester, selenomethionine octyl ester, selenomethionine propyl ester, selenomethionine stearyl ester, selenomethionine tetradecyl ester, selenomethionine tridecyl ester, thiodiglycolic acid, thiodipropionic acid, thioglycerol, isomers and mixtures of isomers thereof, and salts thereof.

Salts of HCA compounds can be acid addition salts such as the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate and undecanoate salts. In a particular embodiment, the hydrochloride salt of one of the compounds individually mentioned above is present in the composition in an antioxidant effective amount.

Without being bound by theory, it is generally believed that heavier-chalcogen antioxidants such as those exemplified above protect the active compound by being themselves more readily oxidizable and, therefore, being oxidized preferentially over the drug compound. In general, for this mode of operation to provide an acceptable degree of protection for the drug compound, an antioxidant of Formula II or Formula III must be present in a substantial amount, for example in a molar ratio to the drug compound of at least about 1:10. In some embodiments, the molar ratio of antioxidant to the drug compound is about 1:10 to about 2:1, for example about 1:5 to about 1.5:1. Best results will sometimes be obtained when the molar ratio is approximately 1:1, i.e., about 8:10 to about 10:8.

This typical requirement for a relatively high antioxidant concentration in the formulation places constraints both on the selection of antioxidant and on the selection of other formulation components. In particular, a carrier system must be selected that is capable of dissolving not only the active agent but also the antioxidant, in an antioxidant effective amount. One of skill in the art can select a suitable lipid carrier, which can comprise a single lipid material or a mixture of two or more such materials, by routine solubility testing based on the disclosure herein.

Notwithstanding the antioxidant efficacy of sulfur-containing antioxidants of Formula II or Formula III, the present inventors have found that, at molar ratios of approximately 1:1, such antioxidants have a tendency to result in solutions that become cloudy upon storage, when ABT-263 is used in the form of its free base. For solutions containing ABT-263 in the form of its bis-HCl salt, this tendency is absent or at least less marked.

However, in yet another unexpected discovery, ABT-263 free base has been found to be less susceptible to sulfoxide formation than ABT-263 bis-HCl when formulated in lipid solution (but in the absence of antioxidant), as shown in Table 6 (see Example 3 hereinbelow). The solvent system in solution A is Phosal 53 MCT™/ethanol, 9:1 v/v; and in solution B is Labrafil M 1944 CS™/oleic acid/polysorbate 80, 30%/40%/30% by weight. (Labrafil M 1944 CS™ of Gattefossé contains polyoxyethylene glyceryl monooleate.) The three-week study was conducted at 40° C. without nitrogen purging of headspace.

To take advantage of the unexpected finding that ABT-263 is less susceptible to sulfoxide formation in its free base than salt form, the present inventors have turned to a different class of sulfur-containing antioxidants, namely inorganic antioxidants of the sulfite, bisulfite, metabisulfite and thiosulfate classes. To complicate matters, these antioxidants are poorly lipid-soluble and must be introduced to the carrier or drug-carrier system in aqueous solution. Presence of water promotes sulfoxide formation in ABT-263 solutions, the very effect that is sought to be minimized. To restrict the amount of added water, poorly lipid-soluble antioxidants are, in one embodiment of the present invention, added at much lower concentrations than those providing molar equivalence to the concentration of ABT-263.

Where a poorly lipid-soluble antioxidant such as a sulfite, bisulfite, metabisulfite or thiosulfate antioxidant is used, it is accompanied in the drug-carrier system by water in an amount not exceeding about 1% by weight, for example about 0.2% to about 0.8% by weight. The amount of such antioxidant that can be introduced in such a small amount of water typically does not exceed about 0.2% by weight, and is for example an amount of about 0.02% to about 0.2%, or about 0.05% to about 0.15%, by weight, of the drug-carrier system.

To minimize the amount of water added to the formulation, it is desirable to provide the antioxidant in the form of a relatively concentrated aqueous stock solution, for example having at least about 10% by weight antioxidant. However, it has been found that where an excessively concentrated stock solution (e.g., about 20% or higher) is used, this can result in undesirable precipitation of solids in the formulation. Suitable concentrations of antioxidant in the stock solution are typically about 10% to about 18%, illustratively about 15%, by weight.

Sodium and potassium salts of sulfites, bisulfites, metabisulfites and thiosulfates are useful antioxidants according to the present embodiment; more particularly sodium and potassium metabisulfites.

To further minimize sulfoxide formation, a chelating agent such as EDTA or a salt thereof (e.g., disodium EDTA or calcium disodium EDTA) is optionally added, for example in an amount of about 0.002% to about 0.02% by weight of the drug-carrier system. EDTA can be added as an aqueous stock solution in the same manner as the antioxidant. The antioxidant and EDTA can, if desired, be added as components of the same stock solution. Chelating agents sequester metal ions that can promote oxidative degradation.

Surprisingly at the very low antioxidant concentrations contemplated herein (typically the molar ratio of poorly lipid-soluble antioxidant to ABT-263 according to the present embodiment is no greater than about 1:20), sulfoxide formation has been found to remain within acceptable limits, as illustrated in Example 12 herein.

Sulfoxide formation can be further minimized by selecting formulation ingredients having low peroxide value. Peroxide value is a well established property of pharmaceutical excipients and is generally expressed (as herein) in units corresponding to milliequivalents of peroxides per kilogram of excipient (meq/kg). Some excipients inherently have low peroxide value, but others, for example those having unsaturated fatty acid such as oleyl moieties and/or polyoxyethylene chains, can be sources of peroxides. In the case of polysorbate 80, for example, it is preferable to select a source of polysorbate 80 having a peroxide value not greater than about 5, for example not greater than about 2. Suitable sources include Crillet 4HP™ and Super-Refined Tween 80™, both available from Croda.

The carrier is "substantially non-aqueous", i.e., having no water, or having an amount of water that is small enough to be, in practical terms, essentially non-deleterious to performance or properties of the composition. Typically, the carrier comprises zero to less than about 5% by weight water. It will be understood that certain ingredients useful herein can bind small amounts of water on or within their molecules or supramolecular structures; such bound water if present does not affect the "substantially non-aqueous" character of the carrier as defined herein. Furthermore, as indicated above, use of a poorly lipid-soluble antioxidant requires that a small amount of water (not more than about 1% by weight of the drug-carrier system) be added; again, this does not affect the "substantially non-aqueous" character of the carrier as defined herein.

In some embodiments, the carrier comprises one or more glyceride materials. Suitable glyceride materials include, without limitation, medium to long chain mono-, di- and triglycerides. The term "medium chain" herein refers to hydrocarbyl chains individually having no less than about 6 and less than about 12 carbon atoms, including for example $C_8$ to $C_{10}$ chains. Thus glyceride materials comprising caprylyl and capryl chains, e.g., caprylic/capric mono-, di- and/or triglycerides, are examples of "medium chain" glyceride materials herein. The term "long chain" herein refers to hydrocarbyl chains individually having at least about 12, for example about 12 to about 18, carbon atoms, including for example lauryl, myristyl, cetyl, stearyl, oleyl, linoleyl and linolenyl chains. Medium to long chain hydrocarbyl groups in the glyceride materials can be saturated, mono- or polyunsaturated.

In one embodiment the carrier comprises a medium chain and/or a long chain triglyceride material. A suitable example of a medium chain triglyceride material is a caprylic/capric triglyceride product such as, for example, Captex 355 EP™ of Abitec Corp. and products substantially equivalent thereto. Suitable examples of long chain triglycerides include any pharmaceutically acceptable vegetable oil, for example canola, coconut, corn, cottonseed, flaxseed, olive, palm, peanut, safflower, sesame, soy and sunflower oils, and mixtures of such oils. Oils of animal, particularly marine animal, origin can also be used, including for example fish oil.

A carrier system that has been found particularly useful in solubilizing both (a) a therapeutically effective amount of a compound of Formula I and (b) an antioxidant effective amount of a heavier-chalcogen antioxidant, comprises two essential components: a phospholipid, and a pharmaceutically acceptable solubilizing agent for the phospholipid. It will be understood that reference in the singular to a (or the) phospholipid, solubilizing agent or other formulation ingredient herein includes the plural; thus combinations, for example mixtures, of more than one phospholipid, or more than one solubilizing agent, are expressly contemplated herein. The solubilizing agent, or the combination of solubilizing agent and phospholipid, also solubilizes the drug and the antioxidant, although other carrier ingredients, such as a surfactant or an alcohol such as ethanol, optionally present in the carrier can in some circumstances provide enhanced solubilization of the drug and antioxidant.

Any pharmaceutically acceptable phospholipid or mixture of phospholipids can be used. In general such phospholipids are phosphoric acid esters that yield on hydrolysis phosphoric acid, fatty acid(s), an alcohol and a nitrogenous base. Pharmaceutically acceptable phospholipids can include without limitation phosphatidylcholines, phosphatidylserines and phosphatidylethanolamines. In one embodiment the composition comprises phosphatidylcholine, derived for example from natural lecithin. Any source of lecithin can be used, including animal sources such as egg yolk, but plant sources are generally preferred. Soy is a particularly rich source of lecithin that can provide phosphatidylcholine for use in the present invention.

Illustratively, a suitable amount of phospholipid is about 15% to about 75%, for example about 30% to about 60%, by weight of the carrier, although greater and lesser amounts can be useful in particular situations.

Ingredients useful as components of the solubilizing agent are not particularly limited and will depend to some extent on the particular drug and antioxidant and the desired concentration of each and of phospholipid. In one embodiment, the solubilizing agent comprises one or more glycols, one or more glycolides and/or one or more glyceride materials.

Glycols are generally suitable only for non-encapsulated formulations or where a soft capsule shell is to be used, and tend to be incompatible with hard shells such as hard gelatin shells. Suitable glycols include propylene glycol and polyethylene glycols (PEGs) having molecular weight of about 200 to about 1,000 g/mol, e.g., PEG-400, which has an average molecular weight of about 400 g/mol. Such glycols can provide relatively high solubility of the drug; however the potential for oxidative degradation of the drug can be increased when in solution in a carrier comprising such glycols, for example because of the tendency of glycols to produce superoxides, peroxides and/or free hydroxyl radicals. The higher the glycol content of the carrier, the greater may be the tendency for degradation of a chemically unstable drug. In one embodiment, therefore, one or more glycols are present in a total glycol amount of at least about 1% but less than about 50%, for example less than about 30%, less than about 20%, less than about 15% or less than about 10% by weight of the carrier. In another embodiment, the carrier comprises substantially no glycol.

Glycolides are glycols such as propylene glycol or PEG esterified with one or more organic acids, for example medium- to long-chain fatty acids. Suitable examples include propylene glycol monocaprylate, propylene glycol monolaurate and propylene glycol dilaurate products such as, for example. Capmul PG-8™, Capmul PG-12™ and Capmul PG-2L™ respectively of Abitec Corp. and products substantially equivalent thereto.

Suitable glyceride materials for use together with a phospholipid include, without limitation, those mentioned above. Where one or more glyceride materials are present as a major component of the solubilizing agent, a suitable total amount of glycerides is an amount effective to solubilize the phospholipid and, in combination with other components of the carrier, effective to maintain the drug and antioxidant in solution. For example, glyceride materials such as medium chain and/or long chain mono-, di- and triglycerides, more typically medium-chain mono-, di- and triglycerides, can be present in a total glyceride amount of about 5% to about 70%, for example about 15% to about 60% or about 25% to about 50%, by weight of the carrier, although greater and lesser amounts can be useful in particular situations. In one embodiment, the encapsulated liquid comprises about 7% to about 30%, for example about 10% to about 25%, by weight medium-chain triglycerides and about 7% to about 30%, for example about 10% to about 25%, by weight medium-chain mono- and diglycerides.

Additional solubilizing agents that are other than glycols, glycolides or glyceride materials can be included if desired. Such agents, for example N-substituted amide solvents such as dimethylformamide (DMF) and N,N-dimethylacetamide (DMA), can, in specific cases, assist in raising the limit of solubility of the drug in the carrier, thereby permitting increased drug loading. However, the carriers useful herein generally provide adequate solubility of small-molecule drugs of interest herein without such additional agents.

Even when a sufficient amount of a glycol, glycolide or glyceride material is present to solubilize the phospholipid, the resulting carrier solution and/or the drug-carrier system may be rather viscous and difficult or inconvenient to handle. In such cases it may be found desirable to include in the carrier a viscosity reducing agent in an amount effective to provide acceptably low viscosity. An example of such an agent is an alcohol, more particularly ethanol, which is preferably introduced in a form that is substantially free of water, for example 99% ethanol, dehydrated alcohol USP or absolute ethanol. Excessively high concentrations of ethanol should, however, generally be avoided. This is particularly true where, for example, the drug-carrier system is to be administered in a gelatin capsule, because of the tendency of high ethanol concentrations to result in mechanical failure of the capsule. In general, suitable amounts of ethanol are 0% to about 25%, for example about 1% to about 20% or about 3% to about 15%, by weight of the carrier. Glycols such as propylene glycol or PEG and medium-chain mono- and diglycerides (for example caprylic/capric mono- and diglycerides) can also be helpful to lower viscosity; where the drug-carrier system is to be encapsulated in a hard capsule such as a hard gelatin capsule, medium-chain mono- and diglycerides are particularly useful in this regard.

Optionally, the carrier further comprises a pharmaceutically acceptable non-phospholipid surfactant. One of skill in the art will be able to select a suitable surfactant for use in a composition of the invention, based on information herein. Such a surfactant can serve various functions, including for example enhancing dispersion of the encapsulated liquid upon release from the capsule in the aqueous environment of the gastrointestinal tract. Thus in one embodiment the non-phospholipid surfactant is a dispersing and/or emulsifying agent that enhances dispersion and/or emulsification of the capsule contents in real or simulated gastrointestinal fluid. Illustratively, a surfactant such as a polysorbate (polyoxyethylene sorbitan ester), e.g., polysorbate 80 (available for example as Tween 80™ from Uniqema), can be included in an amount of 0% to about 30%, for example about 7% to about 30% or about 10% to about 25%, by weight of the carrier. In some embodiments such a surfactant is included in an amount of 0% to about 5%, for example 0% to about 2% or 0% to about 1%, by weight of the carrier.

Conveniently, pre-blended products are available containing a suitable phospholipid+solubilizing agent combination for use in compositions of the present invention. Pre-blended phospholipid+solubilizing agent products can be advantageous in improving ease of preparation of the present compositions.

An illustrative example of a pre-blended phospholipid+solubilizing agent product is Phosal 50 PG™, available from Phospholipid GmbH, Germany, which comprises, by weight, not less than 50% phosphatidylcholine, not more than 6% lysophosphatidylcholine, about 35% propylene glycol, about 3% mono- and diglycerides from sunflower oil, about 2% soy fatty acids, about 2% ethanol, and about 0.2% ascorbyl palmitate.

Another illustrative example is Phosal 53 MCT™, also available from Phospholipid GmbH, which contains, by weight, not less than 53% phosphatidylcholine, not more than 6% lysophosphatidylcholine, about 29% medium chain triglycerides, 3-6% (typically about 5%) ethanol, about 3% mono- and diglycerides from sunflower oil, about 2% oleic acid, and about 0.2% ascorbyl palmitate (reference composition). A product having the above or substantially equivalent composition, whether sold under the Phosal 53 MCT™ brand or otherwise, is generically referred to herein as "phosphatidylcholine+medium chain triglycerides $^{53}/_{29}$". A product having "substantially equivalent composition" in the present context means having a composition sufficiently similar to the reference composition in its ingredient list and relative amounts of ingredients to exhibit no practical difference in properties with respect to utilization of the product herein.

Yet another illustrative example is Lipoid S75™, available from Lipoid GmbH, which contains, by weight, not less than 70% phosphatidylcholine in a solubilizing system. This can be further blended with medium-chain triglycerides, for example in a 30/70 weight/weight mixture, to provide a product ("Lipoid S75™ MCT") containing, by weight, not less than 20% phosphatidylcholine, 2-4% phosphatidylethanolamine, not more than 1.5% lysophosphatidylcholine, and 67-73% medium-chain triglycerides.

Yet another illustrative example is Phosal 50 SA+™, available from Phospholipid GmbH, which contains, by weight, not less than 50% phosphatidylcholine and not more than 6% lysophosphatidylcholine in a solubilizing system comprising safflower oil and other ingredients.

The phosphatidylcholine component of each of these pre-blended products is derived from soy lecithin. Products of substantially equivalent composition may be obtainable from other suppliers.

A pre-blended product such as Phosal 50 PG™, Phosal 53 MCT™, Lipoid S75™ MCT or Phosal 50 SA+™ can, in some embodiments, constitute substantially the entire carrier system (other than the antioxidant as provided herein). In other embodiments, additional ingredients are present, for example medium-chain mono- and/or diglycerides, ethanol (additional to any that may be present in the pre-blended product), a non-phospholipid surfactant such as polysorbate 80, polyethylene glycol and/or other ingredients. Such additional ingredients, if present, are typically included in only minor amounts. Illustratively, phosphatidylcholine+medium chain triglycerides 53/29 can be included in the carrier in an amount of about 50% to 100%, for example about 80% to 100%, by weight of the carrier.

Some pre-blended products, including Phosal 50 PG™ and Phosal 53 MCT™, contain a small amount of ascorbyl palmitate, an antioxidant which does not meet the definition of a heavier-chalcogen antioxidant herein. Presence of ascorbyl palmitate or other non-heavier-chalcogen antioxidant is generally not detrimental, but if desired a pre-blended product without such antioxidant can be used as the carrier herein.

In some embodiments of the invention, the drug-carrier system is dispersible in an aqueous phase to form a non-gelling, substantially non-transparent liquid dispersion. This property can readily be tested by one of skill in the art, for example by adding 1 part of the drug-carrier system to about 20 parts of water with agitation at ambient temperature and assessing gelling behavior and transparency of the resulting dispersion. Compositions having ingredients in relative amounts as indicated herein will generally be found to pass such a test, i.e., to form a liquid dispersion that does not gel and is substantially non-transparent. In "non-gelling" embodiments, the composition does not contain a gel-promoting agent in a gel-promoting effective amount. If gelling behavior is desired, such an agent can be added. A "substantially non-transparent" dispersion is believed to be formed on mixing with an aqueous phase a composition of the invention having any substantial amount of the phospholipid component. However, for clarification it is emphasized that compositions of the invention themselves, being substantially non-aqueous, are generally clear and transparent. In this regard, it is noted that phospholipids tend to form bi- and multilamellar aggregates when placed in an aqueous environment, such aggregates generally being large enough to scatter transmitted light and thereby provide a non-transparent, e.g., cloudy, dispersion. In the case of phosphatidylcholine+medium chain triglycerides 53/29, for example, dispersion in an aqueous environment typically forms not only multilamellar aggregates but also a coarse oil-in-water emulsion. Presence of multilamellar aggregates can often be confirmed by microscopic examination in presence of polarized light, such aggregates tending to exhibit birefringence, for example generating a characteristic "Maltese cross" pattern.

Without being bound by theory, it is believed that behavior of the drug-carrier system of a composition of the invention upon mixing with an aqueous phase is indicative of how the composition interacts with gastrointestinal fluid following oral administration to a subject. Although formation of a gel can be useful for controlled-release topical delivery of a drug, it is believed that gelling would be detrimental to efficient gastrointestinal absorption. For this reason, embodiments of the invention described above, wherein the drug-carrier system does not gel when mixed with an aqueous phase, are generally preferred. It is further believed, again without being bound by theory, that formation of bi- and multilamellar aggregates in the gastrointestinal fluid, as evidenced by non-transparency of the dispersion formed upon mixing the drug-carrier system with an aqueous phase, can be an important factor in providing the relatively high bioavailability of certain compositions of the invention when administered orally.

Illustratively where the drug is ABT-263, the carrier ingredients and amounts thereof are selected to provide solubility of the drug in the carrier of at least about 10 mg/ml, for example at least about 20 mg/ml, at about 25° C.

Optionally, a composition of the present invention further comprises a chelating agent. In some circumstances, a chelating agent such as ethylenediaminetetraacetic acid (EDTA or edetate), carvedilol, citric acid and salts thereof, choline citrate, tartaric acid and salts thereof and the like can further improve storage stability of the formulation. It is believed, without being bound by theory, that a chelating agent can enhance antioxidant effectiveness by sequestering metal ions that catalyze or otherwise promote oxidative degradation of the drug compound.

In one embodiment, EDTA or a salt thereof (e.g., disodium EDTA or calcium disodium EDTA) is optionally added, for example in an amount of about 0.002% to about 0.02% by weight of the drug-carrier system. EDTA can be added as an aqueous stock solution in the same manner as a poorly lipid-soluble antioxidant. The antioxidant and EDTA can, if desired, be added as components of the same stock solution.

Surprisingly at the very low concentrations of poorly lipid-soluble antioxidant such as sodium metabisulfite contemplated herein (typically the molar ratio of such antioxidant to ABT-263 according to the present embodiment is no greater than about 1:20), sulfoxide formation has been found to remain within acceptable limits, as illustrated in Example 12 herein.

Illustratively, a drug-carrier system according to the present embodiment comprises:
about 5% to about 20% by weight ABT-263 free base,
about 15% to about 60% by weight phosphatidylcholine,
about 7% to about 30% by weight of medium-chain triglycerides,
about 7% to about 30% by weight of medium-chain mono- and diglycerides,
about 7% to about 30% polysorbate 80 surfactant,
about 0.02% to about 0.2% by weight sodium or potassium metabisulfite,
about 0.003% to about 0.01% EDTA or salt thereof, and
about 0.2% to about 0.8% water.

Other excipients can optionally be present in the formulation, so long as they do not adversely affect the storage stability, safety or therapeutic efficacy of the formulation to an unacceptable degree. However, in a more particular embodiment, the drug-carrier system consists essentially of the ingredients listed immediately above.

For an encapsulated formulation, the capsule shell can be of any pharmaceutically acceptable material, including hard or soft gelatin. A capsule shell size is selected appropriate to the amount of liquid to be encapsulated. For example, a size 0 capsule shell can be used to encapsulate up to about 600 mg of liquid and a size 00 capsule shell up to about 900 mg of liquid.

A prototype capsule of the present invention comprises a size 0 hard gelatin capsule shell having encapsulated therewithin a liquid solution that comprises:
about 50 mg ABT-263 free base,
about 150 mg phosphatidylcholine,
about 75 mg medium-chain triglycerides,
about 90 mg medium-chain mono- and diglycerides,
about 90 mg polysorbate 80 surfactant,
about 0.25 mg sodium or potassium metabisulfite,
about 0.025 mg EDTA or salt thereof, and
about 2.5 mg water.

The term "about" in the immediately preceding description of a prototype capsule will be understood to mean that the amounts shown can vary within usual manufacturing tolerances accepted in the pharmaceutical industry.

A drug-carrier system of the invention is typically liquid, but can optionally comprise a solid or semi-solid substrate having the drug solution adsorbed therein or thereon. Examples of such substrates include particulate diluents such as lactose, starches, silicon dioxide, etc., and polymers such as polyacrylates, high molecular weight PEGs, or cellulose derivatives, e.g., hydroxypropylmethylcellulose (HPMC). Where a solid solution is desired, a high melting point ingredient such as a wax can be included. A solid drug-carrier system can optionally be encapsulated or, if desired, delivered in tablet form. The drug-carrier system can, in some embodiments, be adsorbed on, or impregnated into, a drug delivery device.

In certain embodiments, the formulation ingredients and amounts thereof are selected to provide enhanced bioabsorption by comparison with a standard solution of the drug, e.g., a solution in a carrier consisting of 10% DMSO in PEG-400, when administered orally. Such enhanced bioabsorption can be evidenced, for example, by a pharmacokinetic (PK) profile having one or more of a higher $C_{max}$ or an increased bioavailability as measured by AUC, for example $AUC_{0-24}$ or $AUC_{0-\infty}$. Illustratively, bioavailability can be expressed as a percentage, for example using the parameter F, which computes AUC for oral delivery of a test composition as a percentage of AUC for intravenous (i.v.) delivery of the drug in a suitable solvent, taking into account any difference between oral and i.v. doses.

Bioavailability can be determined by PK studies in humans or in any suitable model species. For present purposes, a dog model is generally suitable. In various illustrative embodiments, where the drug is ABT-263, compositions of the invention exhibit oral bioavailability of at least about 30%, at least about 35% or at least about 40%, up to or exceeding about 50%, in a dog model, when administered as a single dose of about 2.5 to about 10 mg/kg to fasting or non-fasting animals.

The present invention is not limited by the process used to prepare a composition as embraced or described herein. Any suitable process of pharmacy can be used. Illustratively, compositions of the invention can be prepared by a process comprising simple mixing of the recited ingredients, wherein order of addition is not critical, to form a drug-carrier system. It is noted, however, that if a phospholipid component is used in its solid state, for example in the form of soy lecithin, it will generally be desirable to first solubilize the phospholipid with the solubilizing agent component or part thereof. Thereafter other ingredients of the carrier, if any, the drug and the antioxidant can be added by simple mixing, with agitation as appropriate. As mentioned above, use of a pre-blended product comprising phospholipid and solubilizing agent can simplify preparation of the composition. Optionally, the drug-carrier system can be used as a premix for capsule filling. The term "filling" used in relation to a capsule herein means placement of a desired amount of a composition in a capsule shell, and should not be taken to mean that all space in the capsule is necessarily occupied by the composition.

Where the drug-carrier system comprises a poorly lipid-soluble sulfur-containing antioxidant such as sodium or potassium metabisulfite, the process should be adjusted. An illustrative process for preparing such a drug-carrier system comprises the following steps.

An API that consists essentially of ABT-263 free base or a pharmaceutically acceptable salt thereof (e.g., ABT-263 bis-HCl) is dissolved in a medium comprising the phospholipid and at least a portion of the solubilizing agent to provide a lipid solution of ABT-263. As noted above, a pre-blended product comprising the phospholipid and solubilizing agent can be used as the medium for dissolution of the API.

Where ABT-263 is to be formulated in its free base form, any solid-state form of ABT-263 free base can serve as the API. However, it will generally be found preferable to use a crystalline form of ABT-263 free base as API, for example a solvated or non-solvated crystalline form. In a particular embodiment of the present method, a non-solvated crystalline form such as Form I or Form II crystalline ABT-263 as described herein is used as API.

A non-phospholipid surfactant and, optionally, the balance of the solubilizing agent, is admixed with the solubilizing agent (prior to or simultaneously with dissolution of the API) or with the lipid solution (after dissolution of the API). As noted above, the non-phospholipid surfactant is illustratively a polysorbate such as polysorbate 80. The balance of the solubilizing agent can be the same material as the portion of solubilizing agent used together with the phospholipid to dissolve the ABT-263; alternatively it can be a different material. For example, the portion of solubilizing agent used together with the phospholipid for dissolution of the ABT-863 can comprise one or more medium-chain triglycerides, and the balance of solubilizing agent admixed in the present step can comprise one or more medium-chain mono- and/or diglycerides, for example a caprylic/capric mono- and diglyceride product such as Imwitor 742™.

Separately, a poorly lipid-soluble sulfur-containing antioxidant is dissolved in water to prepare an aqueous stock solution. Stock solutions at about 10% to about 18% by weight concentration will generally be found suitable, as explained above.

The aqueous stock solution is then admixed with the lipid solution, typically after addition of the non-phospholipid surfactant, to provide a liquid solution for encapsulation.

Optionally, the resulting liquid solution is encapsulated in a capsule shell by any known encapsulation process.

Compositions embraced herein, including compositions described generally or with specificity herein, are useful for orally delivering a drug that is a compound of Formula I or a pharmaceutically acceptable salt, prodrug, salt of a prodrug or metabolite thereof to a subject. Accordingly, a method of the invention for delivering such a drug to a subject comprises orally administering a composition as described above.

The subject can be human or non-human (e.g., a farm, zoo, work or companion animal, or a laboratory animal used as a model) but in an important embodiment the subject is a human patient in need of the drug, for example to treat a disease characterized by apoptotic dysfunction and/or over-expression of an anti-apoptotic Bcl-2 family protein. A human subject can be male or female and of any age. The patient is typically an adult, but a method of the invention can be useful to treat a childhood cancer such as leukemia, for example acute lymphocytic leukemia, in a pediatric patient.

The composition is normally administered in an amount providing a therapeutically effective daily dose of the drug. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the particular compound, the subject (including species and body weight of the subject), the disease (e.g., the particular type of cancer) to be treated, the stage and/or severity of the disease, the individual subject's tolerance of the compound, whether the compound is administered in monotherapy or in combination with one or more other drugs, e.g., other chemotherapeutics for treatment of cancer, and other factors. Thus the daily dose can vary within wide margins, for example from about 10 to about 1,000 mg. Greater or lesser daily doses can be appropriate in specific situations. It will be understood that recitation herein of a "therapeutically effective" dose herein does not necessarily require that the drug be therapeutically effective if only a single such dose is administered; typically therapeutic efficacy depends on the composition being administered repeatedly according to a regimen involving appropriate frequency and duration of administration. It is strongly preferred that, while the daily dose selected is sufficient to provide benefit in terms of treating the cancer, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a cancer patient on a course of therapy with a relatively low daily dose and titrate the dose upwards over a period of days or weeks, to reduce risk of adverse side-effects.

Illustratively, suitable doses of ABT-263 are generally about 25 to about 1,000 mg/day, more typically about 50 to about 500 mg/day or about 200 to about 400 mg/day, for example about 50, about 100, about 150, about 200, about 250, about 300, about 350, about 400, about 450 or about 500 mg/day, administered at an average dosage interval of about 3 hours to about 7 days, for example about 8 hours to about 3 days, or about 12 hours to about 2 days. In most cases a once-daily (q.d.) administration regimen is suitable.

An "average dosage interval" herein is defined as a span of time, for example one day or one week, divided by the number of unit doses administered over that span of time. For example, where a drug is administered three times a day, around 8 am, around noon and around 6 pm, the average dosage interval is 8 hours (a 24-hour time span divided by 3). If the drug is formulated as a discrete dosage form such as a tablet or capsule, a plurality (e.g., 2 to about 10) of dosage forms administered at one time is considered a unit dose for the purpose of defining the average dosage interval.

Where the drug compound is ABT-263, for example in the form of ABT-263 free base or ABT-263 bis-HCl, a daily dosage amount and dosage interval can, in some embodiments, be selected to maintain a plasma concentration of ABT-263 in a range of about 0.5 to about 10 µg/ml. Thus, during a course of ABT-263 therapy according to such embodiments, the steady-state peak plasma concentration ($C_{max}$) should in general not exceed about 10 µg/ml, and the steady-state trough plasma concentration ($C_{min}$) should in general not fall below about 0.5 µg/ml. It will further be found desirable to select, within the ranges provided above, a daily dosage amount and average dosage interval effective to provide a $C_{max}/C_{min}$ ratio not greater than about 5, for example not greater than about 3, at steady-state. It will be understood that longer dosage intervals will tend to result in greater $C_{max}/C_{min}$ ratios. Illustratively, at steady-state, an ABT-263 $C_{max}$ of about 3 to about 8 µg/ml and $C_{min}$ of about 1 to about 5 µg/ml can be targeted by the present method. Steady-state values of $C_{max}$ and $C_{min}$ can be established in a human PK study, for example conducted according to standard protocols including but not limited to those acceptable to a regulatory agency such as the U.S. Food and Drug Administration (FDA).

Where the composition is in the form of an unencapsulated liquid, the composition can be swallowed neat, but administration is generally more convenient and pleasant if the composition is first diluted in a suitable imbibable liquid. Suitable liquid diluents include without limitation any aqueous beverage such as water, milk, fruit juice (e.g., apple juice, grape juice, orange juice, etc.), carbonated drink, enteral nutrition formula, energy drink, tea or coffee. Where a liquid diluent is to be used, the composition should be mixed with the diluent using sufficient agitation (e.g., by shaking and/or stirring) to thoroughly disperse the composition in the diluent, and administered immediately thereafter, so that the composition does not separate from the diluent before swallowing. If desired the diluent can be in the form of a part-frozen slurry such as a slush or smoothie. Any convenient rate of dilution can be employed, for example about 1 to about 100, or about 5 to about 50, parts by volume of the composition per part by volume of the diluent.

Where the composition is in the form of a capsule, one to a small plurality of capsules can be swallowed whole, typically with the aid of water or other imbibable liquid to help the swallowing process. Suitable capsule shell materials include, without limitation, gelatin (in the form of hard gelatin capsules or soft elastic gelatin capsules), starch, carrageenan and HPMC. Where the drug-carrier system is liquid, soft elastic gelatin capsules are generally preferred.

For administering ABT-263 according to the present method, the drug is illustratively present in the pharmaceutical composition in the form of ABT-263 free base or ABT-263 bis-HCl. Any ABT-263 composition of the present invention, as defined more fully above, can be used.

As compositions of the present invention typically exhibit only a minor food effect, administration according to the present embodiment can be with or without food, i.e., in a non-fasting or fasting condition. It is generally preferred to administer the present compositions to a non-fasting patient.

Compositions of the invention are suitable for use in monotherapy or in combination therapy, for example with other chemotherapeutics or with ionizing radiation. A particular advantage of the present invention is that it permits once-daily oral administration, a regimen which is convenient for the patient who is undergoing treatment with other orally administered drugs on a once-daily regimen. Oral administration is easily accomplished by the patient him/herself or by a caregiver in the patient's home; it is also a convenient route of administration for patients in a hospital or residential care setting.

Combination therapies illustratively include administration of a composition of the present invention, for example such a composition comprising ABT-263, concomitantly with one or more of bortezomid, carboplatin, cisplatin, cyclophosphamide, dacarbazine, dexamethasone, docetaxel, doxorubicin, etoposide, fludarabine, hydroxydoxorubicin, irinotecan, paclitaxel, rapamycin, rituximab, vincristine and the like, for example with a polytherapy such as CHOP (cyclophosphamide+hydroxydoxorubicin+vincristine+prednisone), RCVP (rituximab+cyclophosphamide+vincristine+prednisone), R-CHOP (rituximab+CHOP) or DA-EPOCH-R (dose-adjusted etoposide, prednisone, vincristine, cyclophosphamide, doxorubicin and rituximab).

A composition of the invention, for example such a composition comprising ABT-263, can be administered in combination therapy with one or more therapeutic agents that include, but are not limited to, angiogenesis inhibitors, antiproliferative agents, other apoptosis promoters (for example, Bcl-xL, Bcl-w and Bfl-1 inhibitors), activators of a death receptor pathway, BiTE (bi-specific T-cell engager) antibodies, dual variable domain binding proteins (DVDs), inhibitors of apoptosis proteins (IAPs), microRNAs, mitogen-activated extracellular signal-regulated kinase inhibitors, multivalent binding proteins, poly-ADP (adenosine diphosphate)-ribose polymerase (PARP) inhibitors, small inhibitory ribonucleic acids (siRNAs), kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDs), antimitotic agents, alkylating agents, antimetabolites, intercalating antibiotics, platinum-containing chemotherapeutic agents, growth factor inhibitors, ionizing radiation, cell cycle inhibitors, enzymes, topoisomerase inhibitors, biologic response modifiers, immunologicals, antibodies, hormonal therapies, retinoids, deltoids, plant alkaloids, proteasome inhibitors, HSP-90 inhibitors, histone deacetylase (HDAC) inhibitors, purine analogs, pyrimidine analogs, MEK inhibitors, CDK inhibitors, ErbB2 receptor inhibitors, mTOR inhibitors as well as other antitumor agents.

Angiogenesis inhibitors include, but are not limited to, EGFR inhibitors, PDGFR inhibitors, VEGFR inhibitors, TIE2 inhibitors, IGF1R inhibitors, matrix metalloproteinase 2 (MMP-2) inhibitors, matrix metalloproteinase 9 (MMP-9) inhibitors and thrombospondin analogs.

Examples of EGFR inhibitors include, but are not limited to, gefitinib, erlotinib, cetuximab, EMD-7200, ABX-EGF, HR3, IgA antibodies, TP-38 (IVAX), EGFR fusion protein, EGF-vaccine, anti-EGFR immunoliposomes and lapatinib.

Examples of PDGFR inhibitors include, but are not limited to, CP-673451 and CP-868596.

Examples of VEGFR inhibitors include, but are not limited to, bevacizumab, sunitinib, sorafenib, CP-547632, axitinib, vandetanib, AEE788, AZD-2171, VEGF trap, vatalanib, pegaptanib, 1M862, pazopanib, ABT-869 and angiozyme.

Bcl-2 family protein inhibitors other than ABT-263 or compounds of Formula I herein include, but are not limited to, AT-101 ((−)gossypol), Genasense™ Bcl-2-targeting antisense oligonucleotide (G3139 or oblimersen), IPI-194, IPI-565, ABT-737, GX-070 (obatoclax) and the like.

Activators of a death receptor pathway include, but are not limited to, TRAIL, antibodies or other agents that target death receptors (e.g., DR4 and DR5) such as apomab, conatumumab, ETR2-ST01, GDC0145 (lexatumumab), HGS-1029, LBY-135, PRO-1762 and trastuzumab.

Examples of thrombospondin analogs include, but are not limited to, TSP-1, ABT-510, ABT-567 and ABT-898.

Examples of aurora kinase inhibitors include, but are not limited to, VX-680, AZD-1152 and MLN-8054.

An example of a polo-like kinase inhibitor includes, but is not limited to, BI-2536.

Examples of bcr-abl kinase inhibitors include, but are not limited to, imatinib and dasatinib.

Examples of platinum-containing agents include, but are not limited to, cisplatin, carboplatin, eptaplatin, lobaplatin, nedaplatin, oxaliplatin and satraplatin.

Examples of mTOR inhibitors include, but are not limited to, CCI-779, rapamycin, temsirolimus, everolimus, RAD001 and AP-23573.

Examples of HSP-90 inhibitors include, but are not limited to, geldanamycin, radicicol, 17-AAG, KOS-953, 17-DMAG, CNF-101, CNF-1010,17-AAG-nab, NCS-683664, efungumab, CNF-2024, PU3, PU24FC1, VER-49009, IPI-504, SNX-2112 and STA-9090.

Examples of HDAC inhibitors include, but are not limited to, suberoylanilide hydroxamic acid (SAHA), MS-275, valproic acid, TSA, LAQ-824, trapoxin and depsipeptide.

Examples of MEK inhibitors include, but are not limited to, PD-325901, ARRY-142886, ARRY-438162 and PD-98059.

Examples of CDK inhibitors include, but are not limited to, flavopyridol, MCS-5A, CVT-2584, seliciclib ZK-304709, PHA-690509, BMI-1040, GPC-286199, BMS-387032, PD-332991 and AZD-5438.

Examples of COX-2 inhibitors include, but are not limited to, celecoxib, parecoxib, deracoxib, ABT-963, etoricoxib, lumiracoxib, BMS-347070, RS 57067, NS-398, valdecoxib, rofecoxib, SD-8381, 4-methyl-2-(3,4-dimethylphenyl)-1-(4-sulfamoylphenyl)-1H-pyrrole, T-614, JTE-522, S-2474, SVT-2016, CT-3 and SC-58125.

Examples of NSAIDs include, but are not limited to, salsalate, diflunisal, ibuprofen, ketoprofen, nabumetone, piroxicam, naproxen, diclofenac, indomethacin, sulindac, tolmetin, etodolac, ketorolac and oxaprozin.

Examples of ErbB2 receptor inhibitors include, but are not limited to, CP-724714, canertinib, trastuzumab, petuzumab, TAK-165, ionafarnib, GW-282974, EKB-569, PI-166, dHER2, APC-8024, anti-HER/2neu bispecific antibody B7.her2IgG3 and HER2 trifunctional bispecific antibodies mAB AR-209 and mAB 2B-1.

Examples of alkylating agents include, but are not limited to, nitrogen mustard N-oxide, cyclophosphamide, ifosfamide, trofosfamide, chlorambucil, melphalan, busulfan, mitobronitol, carboquone, thiotepa, ranimustine, nimustine, Cloretazine™ (laromustine), AMD-473, altretamine, AP-5280, apaziquone, brostallicin, bendamustine, carmustine, estramustine, fotemustine, glufosfamide, KW-2170, mafosfamide, mitolactol, lomustine, treosulfan, dacarbazine and temozolomide.

Examples of antimetabolites include, but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, pemetrexed, gemcitabine, fludarabine, 5-azacitidine, capecitabine, cladribine, clofarabine, decitabine, eflornithine, ethenylcytidine, cytosine arabinoside, hydroxyurea, TS-1, melphalan, nelarabine, nolatrexed, disodium pemetrexed, pentostatin, pelitrexol, raltitrexed, triapine, trimetrexate, vidarabine, mycophenolic acid, ocfosfate, pentostatin, tiazofurin, ribavirin, EICAR, hydroxyurea and deferoxamine.

Examples of antibiotics include, but are not limited to, intercalating antibiotics, aclarubicin, actinomycin D, amrubicin, annamycin, adriamycin, bleomycin, daunorubicin, doxorubicin (including liposomal doxorubicin), elsamitrucin, epirubicin, glarubicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, aclarubicin, amonafide, belotecan, camptothecin, 10-hydroxycamptothecin, 9-amino-camptothecin, amsacrine, dexrazoxane, diflomotecan, irinotecan HCl, edotecarin, epirubicin, etoposide, exatecan, becatecarin, gimatecan, lurtotecan, orathecin, BN-80915, mitoxantrone, pirarubicin, pixantrone, rubitecan, sobuzoxane, SN-38, tafluposide and topotecan.

Examples of antibodies include, but are not limited to, rituximab, cetuximab, bevacizumab, trastuzumab, CD40-specific antibodies and IGF1R-specific antibodies, chTNT-1/B, denosumab, edrecolomab, WX G250, zanolimumab, lintuzumab and ticilimumab.

Examples of hormonal therapies include, but are not limited to, sevelamer carbonate, rilostane, luteinizing hormone releasing hormone, modrastane, exemestane, leuprolide acetate, buserelin, cetrorelix, deslorelin, histrelin, anastrozole, fosrelin, goserelin, degarelix, doxercalciferol, fadrozole, formestane, tamoxifen, arzoxifene, bicalutamide, abarelix, triptorelin, finasteride, fulvestrant, toremifene, raloxifene, trilostane, lasofoxifene, letrozole, flutamide, megesterol, mifepristone, nilutamide, dexamethasone, prednisone and other glucocorticoids.

Examples of retinoids or deltoids include, but are not limited to, seocalcitol, lexacalcitol, fenretinide, aliretinoin, tretinoin, bexarotene and LGD-1550.

Examples of plant alkaloids include, but are not limited to, vincristine, vinblastine, vindesine and vinorelbine.

Examples of proteasome inhibitors include, but are not limited to, bortezomib, MG-132, NPI-0052 and PR-171.

Examples of immunologicals include, but are not limited to, interferons and numerous other immune-enhancing agents. Interferons include interferon alpha, interferon alpha-2a, interferon alpha-2b, interferon beta, interferon gamma-1a, interferon gamma-1b, interferon gamma-n1 and combinations thereof. Other agents include filgrastim, lentinan, sizofilan, BCG live, ubenimex, WF-10 (tetrachlorodecaoxide or TCDO), aldesleukin, alemtuzumab, BAM-002, dacarbazine, daclizumab, denileukin, gemtuzumab ozogamicin, ibritumomab, imiquimod, lenograstim, melanoma vaccine, molgramostim, sargaramostim, tasonermin, tecleukin, thymalasin, tositumomab, Virulizin™ immunotherapeutic of Lorus Pharmaceuticals, Z-100 (specific substance of Maruyama or SSM), Zevalin™ (90Y-ibritumomab tiuxetan), epratuzumab, mitumomab, oregovomab, pemtumomab, Provenge™ (sipuleucel-T), teceleukin, Therocys™ (Bacillus Calmette-Guerin), cytotoxic lymphocyte antigen 4 (CTLA4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include, but are not limited to, krestin, lentinan, sizofuran, picibanil, PF-3512676 and ubenimex.

Examples of pyrimidine analogs include, but are not limited to, 5-fluorouracil, floxuridine, doxifluridine, raltitrexed, cytarabine, cytosine arabinoside, fludarabine, triacetyluridine, troxacitabine and gemcitabine.

Examples of purine analogs include, but are not limited to, mercaptopurine and thioguanine.

Examples of antimitotic agents include, but are not limited to, N-(2-((4-hydroxyphenyl)amino)pyridin-3-yl)-4-methoxybenzenesulfonamide, paclitaxel, docetaxel, larotaxel, epothilone D, PNU-100940, batabulin, ixabepilone, patupilone, XRP-9881, vinflunine and ZK-EPO (synthetic epothilone).

Examples of radiotherapy include, but are not limited to, external beam radiotherapy (XBRT), teletherapy, brachytherapy, sealed-source radiotherapy and unsealed-source radiotherapy.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (Sutton et al. (1997) J. Immunol. 158:5783-5790).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mc1-1 have been shown to enhance the activity of ABT-263 (Tse et al. (2008) Cancer Res. 68:3421-3428 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

PARP inhibitors include, but are not limited to, ABT-888, olaparib, KU-59436, AZD-2281, AG-014699, BSI-201, BGP-15, INO-1001, ONO-2231 and the like.

Additionally or alternatively, a composition of the present invention can be administered in combination therapy with one or more antitumor agents selected from ABT-100, N-acetylcolchinol-O-phosphate, acitretin, AE-941, aglycon protopanaxadiol, arglabin, arsenic trioxide, AS04 adjuvant-adsorbed HPV vaccine, L-asparaginase, atamestane, atrasentan, AVE-8062, bosentan, canfosfamide, Canvaxin™, catumaxomab, CeaVac™ celmoleukin, combrestatin A4P, contusugene ladenovec, Cotara™, cyproterone, deoxycoformycin, dexrazoxane, N,N-diethyl-2-(4-(phenylmethyl)phenoxy)ethanamine, 5,6-dimethylxanthenone-4-acetic acid, docosahexaenoic acid/paclitaxel, discodermolide, efaproxiral, enzastaurin, epothilone B, ethynyluracil, exisulind, falimarev, Gastrimmune™ GMK vaccine, GVAX™, halofuginone, histamine, hydroxycarbamide, ibandronic acid, ibritumomab tiuxetan, IL-13-PE38, inalimarev, interleukin 4, KSB-311, lanreotide, lenalidomide, lonafarnib, lovastatin, 5,10-methylenetetrahydrofolate, mifamurtide, miltefosine, motexafin, oblimersen, OncoVAX™, Osidem™, paclitaxel albumin-stabilized nanoparticle, paclitaxel poliglumex, pamidronate, panitumumab, peginterferon alfa, pegaspargase, phenoxodiol, poly(I)-poly(C12U), procarbazine, ranpirnase, rebimastat, recombinant quadrivalent HPV vaccine, squalamine, staurosporine, STn-KLH vaccine, T4 endonuclase V, tazarotene, 6,6',7,12-tetramethoxy-2,2'-dimethyl-1,3-berbaman, thalidomide, TNFerade™, $^{131}$I-tositumomab, trabectedin, triazone, tumor necrosis factor, Ukrain™, vaccinia-MUC-1 vaccine, L-valine-L-boroproline, Vitaxin™, vitespen, zoledronic acid and zorubicin.

In one embodiment, a composition of the invention, for example such a composition comprising ABT-263, is administered in a therapeutically effective amount to a subject in need thereof to treat a disease during which is overexpressed one or more of antiapoptotic Bcl-2 protein, antiapoptotic Bcl-$X_L$ protein and antiapoptotic Bcl-w protein.

In another embodiment, a composition of the invention, for example such a composition comprising ABT-263, is administered in a therapeutically effective amount to a subject in need thereof to treat a disease of abnormal cell growth and/or dysregulated apoptosis.

Examples of such diseases include, but are not limited to, cancer, mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof.

In a more particular embodiment, a composition of the invention, for example such a composition comprising ABT-263, is administered in a therapeutically effective amount to a subject in need thereof to treat bladder cancer, brain cancer, breast cancer, bone marrow cancer, cervical cancer, chronic lymphocytic leukemia, acute lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small-cell lung cancer, prostate cancer, small-cell lung cancer or spleen cancer.

According to any of these embodiments, the composition is administered in monotherapy or in combination therapy with one or more additional therapeutic agents.

For example, a method for treating mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof in a subject comprises administering to the subject therapeutically effective amounts of (a) a composition of the invention, for example such a composition comprising ABT-263, and (b) one or more of etoposide, vincristine, CHOP, rituximab, rapamycin, R-CHOP, RCVP, DA-EPOCH-R or bortezomib.

In particular embodiments, a composition of the invention, for example such a composition comprising ABT-263, is administered in a therapeutically effective amount to a subject in need thereof in monotherapy or in combination therapy with etoposide, vincristine, CHOP, rituximab, rapamycin, R-CHOP, RCVP, DA-EPOCH-R or bortezomib in a therapeutically effective amount, for treatment of a lymphoid malignancy such as B-cell lymphoma or non-Hodgkin's lymphoma.

In other particular embodiments, a composition of the invention, for example such a composition comprising ABT-263, is administered in a therapeutically effective amount to a subject in need thereof in monotherapy or in combination therapy with etoposide, vincristine, CHOP, rituximab, rapamycin, R-CHOP, RCVP, DA-EPOCH-R or bortezomib in a therapeutically effective amount, for treatment of chronic lymphocytic leukemia or acute lymphocytic leukemia.

The present invention also provides a method for maintaining in bloodstream of a human cancer patient a therapeutically effective plasma concentration of ABT-263 and/or one or more metabolites thereof, comprising administering to the subject a pharmaceutical composition comprising a drug-carrier system that comprises ABT-263 or a pharmaceutically acceptable salt, prodrug, salt of a prodrug or metabolite thereof, in solution in a substantially non-aqueous carrier that comprises a phospholipid component and a pharmaceutically acceptable solubilizing component, in a dosage amount equivalent to about 50 to about 500 mg ABT-263 per day, at an average dosage interval of about 3 hours to about 7 days.

What constitutes a therapeutically effective plasma concentration depends inter alia on the particular cancer present in the patient, the stage, severity and aggressiveness of the cancer, and the outcome sought (e.g., stabilization, reduction in tumor growth, tumor shrinkage, reduced risk of metastasis, etc.). It is strongly preferred that, while the plasma concentration is sufficient to provide benefit in terms of treating the cancer, it should not be sufficient to provoke an adverse side-effect to an unacceptable or intolerable degree.

For treatment of cancer in general and of a lymphoid malignancy such as non-Hodgkin's lymphoma in particular, the plasma concentration of ABT-263 should in most cases be maintained in a range of about 0.5 to about 10 µg/ml. Thus, during a course of ABT-263 therapy, the steady-state $C_{max}$ should in general not exceed about 10 µg/ml, and the steady-state $C_{min}$, should in general not fall below about 0.5 µg/ml. It will further be found desirable to select, within the ranges provided above, a daily dosage amount and average dosage interval effective to provide a $C_{max}/C_{min}$ ratio not greater than about 5, for example not greater than about 3, at steady-state.

It will be understood that longer dosage intervals will tend to result in greater $C_{max}/C_{min}$ ratios. Illustratively, at steady-state, an ABT-263 $C_{max}$ of about 3 to about 8 µg/ml and $C_{min}$, of about 1 to about 5 µg/ml can be targeted by the present method.

A daily dosage amount effective to maintain a therapeutically effective ABT-263 plasma level is, according to the present embodiment, about 50 to about 500 mg. In most cases a suitable daily dosage amount is about 200 to about 400 mg. Illustratively, the daily dosage amount can be for example about 50, about 100, about 150, about 200, about 250, about 300, about 350, about 400, about 450 or about 500 mg.

An average dosage interval effective to maintain a therapeutically effective ABT-263 plasma level is, according to the present embodiment, about 3 hours to about 7 days. In most cases a suitable average dosage interval is about 8 hours to about 3 days, or about 12 hours to about 2 days. A once-daily (q.d.) administration regimen is often suitable.

For the present embodiment, ABT-263 is illustratively present in the pharmaceutical composition in the form of ABT-263 free base or ABT-263 bis-HCl. Any ABT-263 composition of the present invention, as defined more fully above, can be used.

As in other embodiments, administration according to the present embodiment can be with or without food, i.e., in a non-fasting or fasting condition. It is generally preferred to administer the present compositions to a non-fasting patient.

Further information of relevance to the present invention is available in a recently published article by Tse et al. (2008) *Cancer Res.* 68:3421-3428 and supplementary data thereto available at Cancer Research Online (cancerres.aacrjournals.org/). This article and its supplementary data are incorporated in their entirety herein by reference.

EXAMPLES

The following examples are illustrative of the invention or of problems overcome by the invention, but are not to be construed as limiting. Characterization of a particular embodiment as unfavorable or not selected for preparation of a prototype formulation does not necessarily mean that such embodiment is totally inoperative or outside the scope of the invention. One of skill in the art, based on the full disclosure herein, can prepare acceptable formulations even using ingredients shown herein to be suboptimal.

Example 1

Solubility of ABT-263 Parent and Bis-HCl Salt in Lipid Solvents

Solubility of ABT-263 parent (free base, crystalline Form I) and ABT-263 bis-HCl salt was tested in a variety of lipid solvents and solvent mixtures in ambient conditions. Trademarked solvents in this study, unless identified hereinabove, are as follows (substantially equivalent products from other manufacturers can be substituted if available):
  Miglyol 810™ of Sasol: caprylic/capric triglycerides;
  Capmul MCM™ of Abitec: glyceryl caprylate/caprate;
  Captex 300™ of Abitec: caprylic/capric triglycerides;
  Labrafil M 2125 CS™ of Gattefosse: polyoxyethylene glyceryl linoleate;
  Tween 20™ of Uniqema: polysorbate 20;
  Labrasol™ of Gattefossë: polyoxyethylene glyceryl caprylate/caprate;
  Cremophor RH40™: polyoxyethylene (40) hydrogenated castor oil.

"PE-91" is Phosal 53 MCT™+ethanol, 9:1 by volume. "LOT-343" is Labrafil M 1944 CS™+oleic acid+Tween 80™, 30:40:30 by weight.

Solubility data are presented in Table 4. In some cases, indicated in Table 4 by an asterisk (*), solubility was initially high but precipitation occurred upon standing.

TABLE 4

Solubility (mg/g) of ABT-263 parent and bis-HCl salt in lipid solvents

| Solvent | Parent (Form I) | bis-HCl salt |
|---|---|---|
| corn oil | <86 | <104 |
| sesame oil | <75 | <80 |
| castor oil | * | >78.8 |
| Miglyol 810 ™ | <76 | <84 |
| Lipoid S75 ™ MCT | 150-200 | 48.9 |
| Phosal 53 MCT ™ | >300 | n.d. |
| oleic acid | >514 | <498 |
| Imwitor 742 ™ | * | >245 |
| Capmul MCM ™ | * | >321 |
| Capmul PG-8 ™ | * | <43 |
| Capmul PG-12 ™ | * | <39 |
| Captex 300 ™ | * | <52 |
| Labrafil M 1944 CS ™ | >265 | <45 |
| Labrafil M 2125 CS ™ | >290 | <44 |
| PEG-400 | >200 | >278 |
| propylene glycol | * | >337 |
| Tween 20 ™ | >256 | >176 |
| Tween 80 ™ | >256 | >125 |
| Labrasol ™ | >242 | >292 |
| Cremophor RH40 ™ | >226 | n.d. |
| poloxamer 124 | >231 | <41 |
| PE-91 | >250 | 89 |
| LOT-343 | >479 | n.d. | n.d. not determined

Example 2

Miscibility of Ternary Excipient Systems with ABT-263 Parent and Bis-HCl Salt

Ternary systems consisting of two solvents and a surfactant were evaluated for miscibility and drug solubility using 20% by weight ABT-263 free base or 10% by weight ABT-263 bis-HCl salt. Solvents evaluated included Labrafil M 1944 CS™, Imwitor 742™ oleic acid, Capmul PG-8™, Capmul PG-12™, Lauroglycol 90™ (propylene glycol monolaurate, available from Gattefosse) and Phosal 53 MCT™. Surfactants evaluated included Tween 80™, Cremophor RH40™, Gelucire 44/14™ (polyoxyethylene glyceryl laurate, available from Gattefosse) and Labrasol™. Data are presented in Table 5.

TABLE 5

Miscibility of ternary systems and solubility of ABT-263 parent and bis-HCl salt

| Ternary system | % by weight | Miscibility of excipients | ABT-263 solubility | |
|---|---|---|---|---|
| | | | 10% salt | 20% free base |
| Labrafil M 1944 CS ™ | 30:45:25 | ✓ | ✓ | X |
| Imwitor 742 ™ | 40:35:25 | ✓ | ✓ | X |

TABLE 5-continued

Miscibility of ternary systems and solubility of ABT-263 parent and bis-HCl salt

| Ternary system | % by weight | Miscibility of excipients | ABT-263 solubility 10% salt | 20% free base |
|---|---|---|---|---|
| Tween 80 ™ | 30:40:30 | ✓ | ✓ | X |
| (LIT systems) | 40:30:30 | ✓ | ✓ | X |
| Labrafil M 1944 CS ™ | 30:45:25 | ✓ | ✓ | ✓ |
| oleic acid | 40:35:25 | ✓ | ✓ | ✓ |
| Tween 80 ™ | 30:40:30 | ✓ | ✓ | ✓ |
| (LOT systems) | 40:30:30 | ✓ | ✓ | ✓ |
| Capmul PG-8 ™ | 45:30:25 | ✓ | X | X |
| Labrafil M 1944 CS ™ | 35:40:25 | ✓ | X | X |
| Tween 80 ™ | 40:30:30 | ✓ | X | X |
| (C8LT systems) | 30:40:30 | ✓ | X | X |
| Capmul PG-12 ™ | 45:30:25 | ✓ | ✓ | ✓ |
| Labrafil M 1944 CS ™ | 35:40:25 | ✓ | ✓ | ✓ |
| Tween 80 ™ | 40:30:30 | ✓ | ✓ | ✓ |
| (C12LT systems) | 30:40:30 | ✓ | ✓ | ✓ |
| Imwitor 742 ™ | 45:30:25 | X | N/A (vehicle not miscible) | |
| Labrafil M 1944 CS ™ | 35:40:25 | X | N/A (vehicle not miscible) | |
| Cremophor RH40 ™ | 40:30:30 | X | N/A (vehicle not miscible) | |
| (ILC systems) | 30:40:30 | X | N/A (vehicle not miscible) | |
|  | 60:30:10 | ✓ | ✓ | X |
|  | 50:40:10 | ✓ | ✓ | X |
|  | 50:30:20 | ✓ | ✓ | X |
|  | 40:40:20 | ✓ | ✓ | X |
| Labrafil M 1944 CS ™ | 30:45:25 | X | N/A (vehicle not miscible) | |
| oleic acid | 40:35:25 | X | N/A (vehicle not miscible) | |
| Cremophor RH40 ™ | 30:40:30 | X | N/A (vehicle not miscible) | |
| (LOC systems) | 40:30:30 | X | N/A (vehicle not miscible) | |
|  | 30:60:10 | ✓ | ✓ | ✓ |
|  | 40:50:10 | ✓ | ✓ | ✓ |
|  | 30:50:20 | X | N/A (vehicle not miscible) | |
|  | 40:40:20 | X | N/A (vehicle not miscible) | |
| Capmul PG-8 ™ | 45:30:25 | X | N/A (vehicle not miscible) | |
| Labrafil M 1944 CS ™ | 35:40:25 | X | N/A (vehicle not miscible) | |
| Cremophor RH40 ™ | 40:30:30 | X | N/A (vehicle not miscible) | |
| (C8LC systems) | 30:40:30 | X | N/A (vehicle not miscible) | |
|  | 60:30:10 | ✓ | X | X |
|  | 50:40:10 | ✓ | X | X |
|  | 50:30:20 | ✓ | X | X |
|  | 40:40:20 | ✓ | X | X |
| Capmul PG-12 ™ | 45:30:25 | X | N/A (vehicle not miscible) | |
| Labrafil M 1944 CS ™ | 35:40:25 | X | N/A (vehicle not miscible) | |
| Cremophor RH40 ™ | 40:30:30 | X | N/A (vehicle not miscible) | |
| (C12LC systems) | 30:40:30 | X | N/A (vehicle not miscible) | |
| Lauroglycol 90 ™ | 45:30:25 | ✓ | ✓ | ✓ |
| Labrafil M 1944 CS ™ | 35:40:25 | X | N/A (vehicle not miscible) | |
| Cremophor RH40 ™ | 40:30:30 | X | N/A (vehicle not miscible) | |
| (LLC systems) | 30:40:30 | X | N/A (vehicle not miscible) | |
| Imwitor 742 ™ | 60:30:10 | X | N/A (vehicle not miscible) | |
| Labrafil M 1944 CS ™ | 50:40:10 | X | N/A (vehicle not miscible) | |
| Gelucire 44/14 ™ | 50:30:20 | X | N/A (vehicle not miscible) | |
| (ILG systems) | 40:40:20 | X | N/A (vehicle not miscible) | |
| oleic acid | 60:30:10 | X | N/A (vehicle not miscible) | |
| Labrafil M 1944 CS ™ | 50:40:10 | X | N/A (vehicle not miscible) | |
| Gelucire 44/14 ™ | 50:30:20 | X | N/A (vehicle not miscible) | |
| (OLG systems) | 40:40:20 | X | N/A (vehicle not miscible) | |
| Capmul PG-8 ™ | 60:30:10 | X | N/A (vehicle not miscible) | |
| Labrafil M 1944 CS ™ | 50:40:10 | X | N/A (vehicle not miscible) | |
| Gelucire 44/14 | 50:30:20 | X | N/A (vehicle not miscible) | |
| (C8LG systems) | 40:40:20 | X | N/A (vehicle not miscible) | |
| Lauroglycol 90 ™ | 60:30:10 | X | N/A (vehicle not miscible) | |
| Labrafil M 1944 CS ™ | 50:40:10 | X | N/A (vehicle not miscible) | |
| Gelucire 44/14 ™ | 50:30:20 | X | N/A (vehicle not miscible) | |
| (LLG systems) | 40:40:20 | X | N/A (vehicle not miscible) | |
| Imwitor 742 ™ | 60:30:10 | ✓ | ✓ | X |
| Labrafil M 1944 CS ™ | 50:40:10 | ✓ | ✓ | X |
| Labrasol ™ | 50:30:20 | ✓ | ✓ | X |
| (ILL systems) | 40:40:20 | ✓ | ✓ | X |
| oleic acid | 60:30:10 | ✓ | ✓ | ✓ |
| Labrafil M 1944 CS ™ | 50:40:10 | ✓ | ✓ | ✓ |
| Labrasol ™ | 50:30:20 | ✓ | ✓ | ✓ |
| (OLL systems) | 40:40:20 | ✓ | ✓ | ✓ |
| Capmul PG-8 | 60:30:10 | ✓ | X | X |
| Labrafil M 1944 CS ™ | 50:40:10 | ✓ | X | X |
| Labrasol ™ | 50:30:20 | ✓ | X | X |
| (C8LL systems) | 40:40:20 | ✓ | ✓ | ✓ |

TABLE 5-continued

Miscibility of ternary systems and solubility of ABT-263 parent and bis-HCl salt

| Ternary system | % by weight | Miscibility of excipients | ABT-263 solubility 10% salt | 20% free base |
|---|---|---|---|---|
| Lauroglycol 90 ™ | 60:30:10 | ✓ | ✓ | X |
| Labrafil M 1944 CS ™ | 50:40:10 | ✓ | ✓ | X |
| Labrasol ™ | 50:30:20 | ✓ | ✓ | ✓ |
| (LLL systems) | 40:40:20 | ✓ | ✓ | ✓ |

All ternary excipient systems tested containing 10-20% Gelucire 44/14™ exhibited immiscibility. Most systems tested containing greater than 20% Cremophor RH40™ also showed immiscibility. Only in certain systems where the excipients were miscible was ABT-263 in free base or bis-HCl salt form soluble at the concentrations tested.

Data for further ternary systems containing phosphatidylcholine-based excipients are presented in Example 8, Tables 10 and 11.

Example 3

Chemical Stability of ABT-263 Free Base and Bis-HCl Salt in Lipid Solution

Preliminary stability studies were conducted to allow a side-by-side comparison between lipid solutions of ABT-263 in bis-HCl salt and free base form. ABT-263 was dissolved in two separate sets of lipid vehicles, Phosal 53 MCT™/ethanol (9:1 by volume; "PE-91") and Labrafil M 1944 CS™/oleic acid/Tween 80™ (30:40:30 by weight; "LOT-343"). No antioxidant was included, nor was headspace nitrogen purging performed. After aging of samples at 40° C. (stress condition) for up to 3 weeks, analysis of total sulfoxides indicated that free base was significantly more stable than bis-HCl salt in the solutions tested (Table 6). Total degradant levels also showed a similar trend (data not shown). The increase in degradant level was accompanied by color change. The bis-HCl salt solutions upon aging showed pronounced color darkening whereas the free base solutions exhibited very little color change.

TABLE 6

Sulfoxide formation in lipid solutions of ABT-263 free base and bis-HCl salt

| | % w/w total sulfoxides | | | |
|---|---|---|---|---|
| | Solution A | | Solution B | |
| Time (weeks) | free base 25 mg/ml | bis-HCl salt 25 mg/ml | free base 100 mg/ml | bis-HCl salt 100 mg/ml |
| 0 | 0.05 | 0.07 | 2.49 | 2.24 |
| 1 | 0.27 | 0.79 | 3.70 | 7.15 |
| 2 | 0.53 | 1.90 | 4.11 | 37.52 |
| 3 | 0.84 | 3.44 | no data | no data |

Example 4

Chemical Stability of ABT-263 Free Base in Various Lipid Solutions

The chemical stability of the ABT-263 free base in solution in various lipid excipients was assessed by conducting a two-week stress test at 40° C., without antioxidant or nitrogen purging. Results are presented in Table 7.

TABLE 7

Sulfoxide formation in lipid solutions of ABT-263 free base

| | Concentration | % w/w total sulfoxides* | | |
|---|---|---|---|---|
| Lipid solvent | (mg/g) | Initial | 1 week | 2 weeks |
| Lipoid S75 ™ MCT | 100 | 0.21 | 0.33 | 0.51 |
| Imwitor 742 ™ | 25** | 0.25 | 0.20 | 0.14 |
| Capmul PG-8 ™ | 25** | 0.21 | 0.25 | 0.19 |
| Tween 80 ™ | 100 | 0.20 | 0.59 | 0.84 |
| Crillet 4HP ™ | 100 | 0.18 | 0.44 | 0.64 |
| Plurol Oleique CC497 ™*/ Lipoid S75 ™ MCT 50:50 v/v | 50 | 0.31 | 2.41 | 6.26 |
| Labrafil M 1944 CS ™ | 100 | 0.30 | 5.86 | 9.16 |
| oleic acid (super-refined) | 100 | 0.04 | 0.18 | 0.29 |
| Phosal 53 MCT ™/ ethanol 9:1 v/v | 50 | n.d. | 0.14 | 0.18 |

*sulfoxide was analyzed as peak % relative to that of ABT-263
**lower concentration was used due to low drug solubility in the lipid vehicle
***polyglyceryl oleate, available from Gattefosse
n.d. not detectable The following can be summarized from the above study.

Very little or only slight growth of sulfoxides was seen in phosphatidylcholine-based lipid excipients such as Phosal 53 MCT™ or Lipoid S75™ MCT.

Very little or only slight growth of sulfoxides was seen in Imwitor 742™, Capmul PG-8™ and oleic acid (super-refined grade).

Moderate sulfoxide growth was seen in Tween 80™. The degradation was slowed down when a purer grade of polysorbate 80 (Crillet 4HP™) was used.

Labrafil M 1944 CS™ and Plurol Oleique CC497™ were both associated with significant degradation of the ABT-263. Both these excipients contain oleic acid in their structure, and the unsaturated nature of oleic acid is known to promote oxidative reaction. This may be the reason for the chemical instability of the drug in these excipients.

Example 5

Chemical Stability of ABT-263 Free Base in Ternary Lipid Solution Systems

Although ABT-263 appeared to be stable in super-refined oleic acid during the two-week stressed test of Example 4, a subsequent test using multicomponent vehicles showed that drug solutions containing oleic acid led to color change upon standing. A comparative storage study was conducted at ambient temperature using solutions of ABT-263 in Imwitor 742™/oleic acid/Tween 80™ (30:40:30 by weight; "IOT-343") and Imwitor 742™/Phosal 53 MCT™/Tween 80™ (40:40:20 by weight; "IPT-442"). The IOT-343 vehicle itself was colorless, and adding ABT-263 free base at 10% by weight to the vehicle only made it very slightly yellow-hued, but the color of the resulting ABT-263 solution darkened significantly upon storage. This was in contrast to a solution of ABT-263 free base at 10% by weight in IPT-442 solution, which had a yellow colored vehicle to begin with, but only darkened slightly upon storage. HPLC analysis for the two drug solutions after storage at ambient conditions for 3 months confirmed that the color change correlated to degradation (total sulfoxide levels were 1.3% for the IOT-343 system and 0.5% for the IPT-442 system). Therefore, oleic acid was excluded from lipid excipients to be used for ABT-263 liquid-filled capsule formulation.

Further stress testing on ABT-263 free base lipid solutions using different ternary lipid combinations showed that Labrafil M 1944 CS™ was also associated with significant oxidative degradation of ABT-263. As shown by results from a three-week stress test presented in Table 8, formulations containing Labrafil M 1944 CS™ showed significant sulfoxide growth upon storage at 40° C. without antioxidant or nitrogen purging. On the other hand, an Imwitor 742™/Phosal 53 MCT™/Tween 80™ (20:50:30 by weight; "IPT-253") solution of ABT-263 which had neither oleic acid nor Labrafil M 1944 CS™ showed much enhanced chemical stability compared to the other formulations tested, namely Labrafil M 1944 CS™/oleic acid/Tween 80™ (30:40:30 by weight; "LOT-343") and Labrafil M 1944 CS™/Imwitor 742™/Tween 80™ (40:30:30 by weight; "LIT-433"). Therefore, both Labrafil M 1944 CS™ as well as oleic acid was excluded from lipid excipients to be used for ABT-263 liquid-filled capsule formulation.

TABLE 8

Sulfoxide formation in ternary lipid solutions of ABT-263 free base

| Ternary lipid solvent system | Concentration (mg/g) | % w/w total sulfoxides* | | | |
|---|---|---|---|---|---|
| | | Initial | 1 week | 2 weeks | 3 weeks |
| LOT-343 | 100 | 2.49 | 3.70 | 4.11 | no data |
| LIT-433 | 100 | 0.21 | 3.20 | 5.13 | no data |
| LIT-433 | 150 | 0.23 | 2.28 | 3.61 | 3.80 |
| IPT-253 | 150 | n.d. | 0.26 | 0.47 | 0.56 |

*sulfoxide was analyzed as peak % relative to that of ABT-263
n.d. not detectable Example 6

Antioxidant Testing for ABT-263 Free Base in Lipid Solution Systems

The effectiveness of different antioxidants in inhibiting oxidative degradation was evaluated in lipid solutions containing ABT-263 free base at 100 mg/g in two different lipid solution systems: (1) Lipoid S75™ MCT and (2) a ternary lipid system (LIT-433; see above). The latter was purposely chosen as a system promoting significant degradation in a short time, as an antioxidant screen. Sulfoxide formation during the two-week stress test at 40° C. with nitrogen purging is shown in Table 9.

TABLE 9

Effect of antioxidants on sulfoxide formation in solutions of ABT-263 free base

| | | % w/w total sulfoxides* | | | | | |
|---|---|---|---|---|---|---|---|
| | Antioxidant | In Lipoid S75 ™ MCT | | | In LIT-433 | | |
| Antioxidant | concentration | Initial | 1 week | 2 weeks | Initial | 1 week | 2 weeks |
| none | | 0.06 | 0.42 | 0.68 | 0.21 | 3.20 | 5.13 |
| ascorbyl palmitate | 100% molar** | n.d. | n.d. | n.d. | 0.31 | 1.37 | 2.07 |
| BHA | 100% molar** | 0.13 | 0.26 | 0.30 | 0.43 | 2.25 | 3.66 |
| BHT | 100% molar** | 0.08 | 0.17 | 0.27 | 0.37 | 2.07 | 3.40 |
| Na metabisulfite*** | 0.1% (w/w) | cloudy solution | | | 0.18 | 1.95 | 3.07 |
| Na thiosulfate*** | 0.1% (w/w) | cloudy solution | | | 0.18 | 2.64 | 4.31 |
| thioglycerol | 100% molar** | 0.08 | 0.09 | 0.13 | 0.33 | 0.50 | 0.56 |
| α-tocopherols | 145% molar** | 0.20 | 0.27 | 0.50 | 0.41 | 3.99 | 9.23 | n.d. not determined (ascorbyl palmitate could not be dissolved at 100% relative molar concentration in this solvent)
*sulfoxide was analyzed as peak % relative to that of ABT-263
**molar concentration relative to ABT-263
***an aqueous stock solution of 15% w/v was prepared for antioxidant addition.

ABT-263 free base degraded to a much lesser extent in the Lipoid S75™ MCT vehicle than in the LIT-433 vehicle system. Thioglycerol provided effective inhibition of drug oxidation in both vehicle systems. In the LIT-433 vehicle system, ascorbyl palmitate, butylated hydroxyanisole (BHA), butylated hydroxytoluene (BHT), sodium metabisulfite and sodium thiosulfate inhibited oxidative degradation to some extent at the concentrations tested, but α-tocopherols were ineffective. It is noted that the concentrations of sodium metabisulfite and sodium thiosulfate were very much lower than those providing molar equivalence to ABT-263. Even at the low concentrations used, the addition of water with these antioxidants led to cloudy solutions. The concentrations of ascorbyl palmitate, BHA and BHT were much higher than typically used for antioxidant purposes.

Example 7

BHA as an Antioxidant for ABT-263 Free Base in Ternary Lipid Solution Systems

Due to its favorable lipophilic nature and wide use in lipid system as an antioxidant, the antioxidant effectiveness of BHA was tested, at a concentration more typical for BHA, in two additional ternary vehicle systems, IPT-253 and LIT-433, containing ABT-263 at 150 mg/g. Testing was done in stress conditions at 40° C. without nitrogen purging. As shown in Table 10, in both systems, addition of 0.2% w/w BHA did not provide any inhibition of sulfoxide formation. It was concluded that free-radical-scavenger types of antioxidant such as BHA and BHT do not appear to be useful in protecting ABT-263 from oxidative degradation in lipid solutions.

TABLE 10

Effect of BHA on sulfoxide formation in solutions of ABT-263 free base

| Ternary system | Antioxidant | % w/w total sulfoxides | | | | |
|---|---|---|---|---|---|---|
| | | Initial | 1 week | 2 weeks | 3 weeks | 4 weeks |
| IPT-253 | none | n.d. | 0.26 | 0.47 | 0.56 | 0.67 |
| | 0.2% w/w BHA | 0.06 | 0.29 | 0.49 | 0.58 | 0.68 |
| LIT-433 | none | 0.23 | 2.28 | 3.61 | 3.86 | 4.19 |
| | 0.2% w/w BHA | 0.24 | 2.22 | 3.54 | 3.80 | 4.19 | n.d. not detectable

Example 8

Phospholipid Solution Systems for ABT-263 Free Base

Based on the above studies, the phosphatidylcholine-containing excipients Phosal 53 MCT™ and Lipoid S75™ MCT were concluded to provide good chemical stability and drug solubility for ABT-263 free base. However, these pre-blended excipients are not suitable for use alone as a vehicle for an ABT-263 liquid-filled capsule, due to either high viscosity (Phosal 53 MCT™) or insufficient drug solubility (Lipoid S75™ MCT). Polysorbate 80 could be used to enhance drug solubility in the vehicle. Excipients such as Capmul PG-8™ or Imwitor 742™ could be used to reduce viscosity of the lipid solution. Both were shown to be chemically compatible with ABT-263. Imwitor 742™ was preferred over Capmul PG-8™ based on previous experience in FDA approved drug products.

Consequently, in developing a prototype liquid-filled capsule, attention focused on excipients such as Phosal 53 MCT™, Lipoid S75™ MCT, polysorbate 80 (the purer forms such as Crillet 4HP™ and super-refined Tween 80™ being preferred) and Imwitor 742™

Two ternary lipid vehicle systems containing either Imwitor 742™/Phosal 53 MCT™/Tween 80™ (abbreviated as "IPT") systems or Imwitor 742™/Lipoid S75™ MCT/Tween 80™ (abbreviated as "IST") systems at various excipient ratios were investigated in a screen for prototype capsule formulations. The level of Imwitor 742™ in the ternary blend was limited to no more than 40%, and the level of polysorbate 80 to no more than 20%. The three-digit suffix following "IPT" or "IST" refers to the respective percentages of the three excipient ingredients, in each case omitting the final zero.

Selection of prototype formulations was based on vehicle miscibility, ABT-263 free base solubility in the vehicle, viscosity of the resulting solution (judged by severity of stringing when released from a dropper) and self-dispersing property of the drug solution (at 10% by weight drug loading), as summarized in Tables 11 and 12 for IPT and IST systems respectively. Schematic phase diagrams for IPT and IST systems (FIGS. 1 and 2) further illustrate the selection process.

As can be seen from Tables 11 and 12 and the phase diagrams in FIGS. 1 and 2, the IPT systems in general provided better vehicle miscibility, drug solubility and dispersibility than the corresponding IST systems. IPT-262 and IST-262 (later replaced by IST-172) were selected as prototype vehicle systems, based on the following rationales.

A phosphatidylcholine-based solvent (for example in the form of Phosal 53 MCT™ or Lipoid S75™ MCT) is needed to ensure both chemical stability (and bioavailability—see below) of the capsule formulation. The amount of such solvent is virtually unlimited due to the low toxicity and high tolerance of lecithin used in oral products.

Polysorbate 80 (especially grades of high purity) is needed to facilitate drug solubility in the vehicle and to enhance self-dispersibility of the lipid formulation. Based on a typical daily dose of ABT-263 (e.g., 200-250 mg) and a maximum daily dose of polysorbate 80 (418 mg), it is reasonable to limit the level of polysorbate 80 to no more than 20% in the vehicle for a prototype formulation with 10% drug loading. Higher levels of polysorbate 80 are also unfavorable due to chemical stability considerations.

In the IPT systems, Imwitor 742™ is needed to reduce the viscosity of the final drug solution to a level that allows for machine capsule filling. In the IST system, Imwitor 742™ is also needed to enhance the miscibility of the vehicle system, since Lipoid S75™ MCT and polysorbate 80 are not miscible at all ratios. However, the amount of Imwitor 742™ is limited to no more than 20% in both prototype systems.

It will be noted from Table 12 that the IST-172 system exhibits poor vehicle miscibility. However, it was found that upon addition of ABT-263 free base the miscibility of the entire system was acceptable; thus the IST-172 formulation became an acceptable prototype liquid for encapsulation.

TABLE 11

Formulation properties of IPT systems containing 10% ABT-263 free base

| Vehicle | Vehicle miscibility | Drug solubility | Stringing* | Dispersibility (description) |
|---|---|---|---|---|
| IPT-190 | ✓ | ✓ | ++ | Dispersed with vigorous shaking |
| IPT-280 | ✓ | ✓ | ++ | Dispersed with vigorous shaking |
| IPT-370 | ✓ | ✓ | ++ | Dispersed with gentle shaking |
| IPT-460 | ✓ | ✓ | + | Dispersed with gentle shaking |
| IPT-091 | ✓ | ✓ | +++ | Dispersed with vigorous shaking |
| IPT-181 | ✓ | ✓ | ++ | Dispersed with vigorous shaking |
| IPT-271 | ✓ | ✓ | + | Dispersed with vigorous shaking |
| IPT-361 | ✓ | ✓ | + | Dispersed with vigorous shaking |
| IPT-451 | ✓ | ✓ | − | Dispersed with gentle shaking |
| IPT-082 | ✓ | ✓ | +++ | Dispersed with vigorous shaking |
| IPT-172 | ✓ | ✓ | ++ | Dispersed with gentle shaking |
| IPT-262 | ✓ | ✓ | + | Dispersed with gentle shaking |
| IPT-352 | ✓ | ✓ | + | Dispersed with gentle shaking |
| IPT-442 | ✓ | ✓ | − | Dispersed with gentle shaking |

✓ vehicle miscible, or drug fully dissolved in vehicle
*stringing: +++ extreme; ++ significant; + slight; − none

TABLE 12

Formulation properties of IST systems containing 10% ABT-263 free base

| Vehicle | Vehicle miscibility | Drug solubility | Stringing* | Dispersibility (description) |
|---|---|---|---|---|
| IST-190 | ✓ | ✓ | − | Oil drops spread but did not disperse until shaken vigorously |
| IST-280 | ✓ | ✓ | − | Oil drops spread but did not disperse until shaken vigorously |
| IST-370 | ✓ | X | n/a | n/a |
| IST-460 | ✓ | X | n/a | n/a |
| IST-091 | X | ✓ | n/a | n/a |
| IST-181 | X | ✓ | − | Dispersed with gentle shaking |
| IST-271 | ✓ | ✓ | − | Dispersed with gentle shaking |
| IST-361 | ✓ | X | n/a | n/a |
| IST-451 | ✓ | X | n/a | n/a |
| IST-082 | X | n/a | n/a | n/a |
| IST-172 | X | ✓ | ++ | Rapidly dispersed with gentle shaking |
| IST-262 | ✓ | ✓ | + | Rapidly dispersed with gentle shaking |
| IST-352 | ✓ | ✓ | + | Dispersed with gentle shaking |
| IST-442 | ✓ | X | n/a | n/a |

✓ vehicle miscible, or drug fully dissolved in vehicle
X vehicle immiscible or miscible but turbid, or residual solids present (due to undissolved drug or precipitation)
n/a solution not made due to immiscible vehicle, or dispersibility test not performed due to undissolved drug
*stringing: +++ extreme; ++ significant; + slight; − none Example 9

Antioxidant Selection for Phospholipid-Based Solutions of ABT-263 Free Base

Based on initial antioxidant screening (see Example 6), accelerated stability studies were further conducted on the two prototype formulations using either sodium metabisulfite (NaMTBS) or thioglycerol as an antioxidant, together with 0.01% EDTA.

The solubility of neat NaMTBS in IPT-262 and IST-262 solutions containing 10% ABT-263 free base and 0.01% EDTA (as edetate calcium disodium) was assessed. After 5 days of rotary mixing under ambient temperature conditions, solids remained in all solutions, at NaMTBS solid concentrations as low as 0.05% w/w (or approximately 2% molar concentration relative to ABT-263).

Due to poor lipid solubility of NaMTBS, an alternative way of introducing it to the lipid solution is by adding a concentrated aqueous stock solution of NaMTBS to the lipid solution. For example, a clear solution was obtained when a 50 mg/ml free base solution in Phosal 53 MCT™/ethanol 9:1 v/v was spiked with a 15% w/v NaMTBS solution up to a final NaMTBS concentration of 9.67 mg/ml (or 100% molar concentration relative to ABT-263). However, as the final concentration of NaMTBS was increased to 150% relative molar concentration or higher, using the 15% w/v stock solution, the lipid solution turned turbid. Using a stock solution at a concentration greater than 20% also results in solution turbidity, indicating that both excess amounts of water and NaMTBS can lead to a cloudy solution.

Example 10

Sulfoxide Formation in Phospholipid-Based Formulations Containing Antioxidant

Results from a two-week accelerated stability study (stress condition: 40° C., with nitrogen purging), as shown in Table 13, indicated that thioglycerol is not as effective as NaMTBS in inhibiting sulfoxide formation in both prototype formulations.

However, the study results also showed that water added with the NaMTBS can negatively impact chemical stability of the drug solution, and this has been shown to be the case regardless of the ABT-263 form (free base or bis-HCl salt) or the vehicle system used (see Table 14; two-week study at 40° C., with nitrogen purging). For this reason, a final concentration of 0.05% (w/w) NaMTBS was selected, and the concentration of MTBS stock solution should also be kept below about 15% w/v in order to avoid turbidity.

TABLE 13

Sulfoxide formation in ABT-263 prototype liquids for encapsulation

| | | % water | % w/w total sulfoxides | | |
|---|---|---|---|---|---|
| Vehicle | Antioxidant | added* | Initial | 1 week | 2 weeks |
| IST-172 | none | 0 | 0.06 | 0.34 | 0.54 |
| IST-172 | 0.05% NaMTBS + 0.01% EDTA | 0.32 | 0.19 | 0.28 | 0.22 |
| IST-172 | 0.55% Thioglycerol + 0.01% EDTA | 0 | 0.22 | 0.27 | 0.55 |
| IPT-262 | none | 0 | 0.14 | 0.41 | 0.55 |
| IPT-262 | 0.05% NaMTBS + 0.01% EDTA | 0.32 | 0.43 | 0.31 | 0.23 |
| IPT-262 | 0.55% Thioglycerol + 0.01% EDTA | 0 | 0.11 | 0.26 | 0.42 |

*water as % of formulation contributed by 15% w/v NaMTBS stock solution

TABLE 14

Sulfoxide formation in ABT-263 lipid solutions: effects of NaMTBS and water

| Vehicle | ABT-263 form | ABT-263 concentration | Antioxidant | Water % | % w/w total sulfoxides |
|---|---|---|---|---|---|
| PE-91 | free base (Form I) | 50 mg/ml | none | 0 | 0.47 |
| PE-91 | free base (Form I) | 50 mg/ml | none | 3.00 | 0.66 |
| PE-91 | bis-HCl salt | 50 mg/ml | none | 0 | 1.90 |
| PE-91 | bis-HCl salt | 50 mg/ml | 0.05% NaMTBS + 0.01% EDTA | 0.32 | 0.53 |
| PE-91 | bis-HCl salt | 50 mg/ml | 0.1% NaMTBS + 0.01% EDTA | 0.61 | 0.84 |
| PE-91 | bis-HCl salt | 50 mg/ml | 0.2% NaMTBS + 0.01% EDTA | 1.17 | 0.97 |

TABLE 14-continued

Sulfoxide formation in ABT-263 lipid solutions: effects of NaMTBS and water

| Vehicle | ABT-263 form | ABT-263 concentration | Antioxidant | Water % | % w/w total sulfoxides |
|---|---|---|---|---|---|
| IST-172 | free base (Form I) | 100 mg/g | none | 0 | 0.54 |
| IST-172 | free base (Form I) | 100 mg/g | 0.05% NaMTBS + 0.01% EDTA | 0.32 | 0.22 |
| IST-172 | free base (Form I) | 100 mg/g | 0.1% NaMTBS + 0.01% EDTA | 0.61 | 0.22 |
| IST-172 | free base (Form I) | 100 mg/g | 0.2% NaMTBS + 0.01% EDTA | 1.17 | 0.58 |
| IPT-262 | free base (Form I) | 100 mg/g | none | 0 | 0.55 |
| IPT-262 | free base (Form I) | 100 mg/g | 0.05% NaMTBS + 0.01% EDTA | 0.32 | 0.23 |
| IPT-262 | free base (Form I) | 100 mg/g | 0.1% NaMTBS + 0.01% EDTA | 0.61 | 0.37 |
| IPT-262 | free base (Form I) | 100 mg/g | 0.2% NaMTBS + 0.01% EDTA | 1.17 | 0.58 |

Example 11

In Vivo Pharmacokinetics of Prototype Liquid-Filled Capsules

Two 100 mg/g ABT-263 free base liquid-filled capsule prototype formulations were dosed in dogs (single-dose, non-fasting conditions) to evaluate their in vivo pharmacokinetics in comparison with 50 mg/ml oral solutions of ABT-263 free base and bis-HCl salt in Phosal 53 MCT™/ethanol 9:1 v/v with 0.01% EDTA.

Each formulation was evaluated in a group of six dogs at a dose of 50 mg/dog. Formulations A (IPT-262) and B (IST-262) were dosed in the same group of dogs in a sequential manner, and Formulations C and D were dosed in a separate group of dogs in a sequential manner. The dogs were fasted overnight prior to dosing, but food was provided 30 minutes prior to dosing. Plasma concentrations of parent drug were determined by HPLC-MS/MS at the completion of each study. Results are presented in Table 15.

The peak concentration ($C_{max}$) of formulation A in plasma was slightly lower than that of formulation B, but AUC of formulation A was higher than that of formulation B, apparently due to slower absorption. Formulation B showed a more consistent but shorter $T_{max}$ of 2-3 hours after dosing. Liquid-filled capsule formulation A gave comparable plasma $C_{max}$, AUC and bioavailability (F %) to that of the oral solutions (Formulations C and D). Based on these results, the IPT-262 prototype (formulation A) was selected as a liquid-filled capsule formulation for human clinical studies.

TABLE 15

Dog pharmacokinetics of prototype liquid-filled capsules (A and B) versus comparative liquid formulations (C and D)

| Formulation | $C_{max}$ (µg/ml) | $T_{max}$ (h) | AUC (µg · h/ml) | F % |
|---|---|---|---|---|
| A | 9.8 | 4.7 | 98.6 | 41.9 |
| B | 11.0 | 2.5 | 76.8 | 31.8 |
| C | 11.3 | 6.0 | 107.8 | 42.5 |
| D | 11.9 | 4.5 | 94.1 | 37.7 |

Example 12

Storage Stability of Prototype Formulations with and without NaMTBS

Preliminary physical and chemical stability results have been obtained on two laboratory-scale batches of a prototype ABT-263 liquid-filled capsule formulation. The only difference between the two batches is presence or absence of antioxidant (sodium metabisulfite). Composition of the two batches is shown in Table 16.

TABLE 16

Composition of prototype liquid for capsules used in stability study

| Component | Batch 1 (with antioxidant) | | Batch 2 (without antioxidant) | |
|---|---|---|---|---|
| | mg per capsule | % w/w | mg per capsule | % w/w |
| ABT-263 free base | 50.0 | 10.0 | 50.0 | 10.0 |
| sodium metabisulfite | 0.25 | 0.05 | — | — |
| edetate calcium disodium | 0.025 | 0.005 | 0.025 | 0.005 |
| water* | 2.48 | 0.50 | 0.23 | 0.05 |
| Phosal 53 MCT ™ | 268.35 | 53.67 | 269.85 | 53.97 |
| Mono- and dicaprylic/ capric glycerides | 89.45 | 17.89 | 89.95 | 17.99 |
| polysorbate 80 | 89.45 | 17.89 | 89.95 | 17.99 |
| Total | 500.0 | 100.0 | 500.0 | 100.0 |

*includes water added with sodium metabisulfite and edetate calcium disodium only The liquids having the composition shown in Table 16 were encapsulated in size 0 hard gelatin capsules and the capsules placed in blister packaging for a chemical stability study. Data after one month storage under various conditions are presented in Table 17. Water content shown in Table 17 is as determined by analysis, and is not directly related to amount of water added with NaMTBS and edetate calcium disodium as in Table 16.

TABLE 17

Chemical stability results for prototype capsules with and without antioxidant

| Batch | Storage conditions | Initial | | | 1 month | | |
|---|---|---|---|---|---|---|---|
| | | total sulfoxides | total degradants | water content (%)* | total sulfoxides | total degradants | water content (%) |
| 1 (with antioxidant) | 5° C. | n.d. | 0.03% | 2.7 | n.d. | 0.03% | 3.1 |
| | 25° C. 60% RH | n.d. | 0.03% | 2.7 | n.d. | 0.06% | 3.6 |
| | 40° C. 75% RH | n.d. | 0.03% | 2.7 | n.d. | 0.03% | 4.8 |
| 2 (without antioxidant) | 5° C. | 0.08% | 0.14% | 3.2 | 0.12% | 0.17% | 3.3 |
| | 25° C. 60% RH | 0.08% | 0.14% | 3.2 | 0.08% | 0.11% | 3.1 |
| | 40° C. 75% RH | 0.08% | 0.14% | 3.2 | 0.29% | 0.42% | 3.8 |

*Initial water content of fill solution: 0.4% for batch 1; 0.2% for batch 2
n.d. not detectable It can be seen from Table 17 that addition of the antioxidant sodium metabisulfite significantly inhibited formation of total sulfoxides, especially under stress storage conditions of 40° C. and 75% RH.

What is claimed is:

1. A pharmaceutical composition in a form of a liquid solution comprising about 5% to about 20% by weight ABT-263 free base, about 15% to about 60% by weight phosphatidylcholine, about 7% to about 30% by weight medium-chain triglycerides, about 7% to about 30% by weight medium-chain mono- and di-glycerides, about 7% to about 30% polysorbate 80 surfactant, about 0.02% to about 0.2% by weight sodium or potassium metabisulfite, about 0.003% to about 0.01% EDTA or salt thereof, and about 0.2% to about 0.8% water.

2. The composition of claim 1, further comprising a capsule shell wherein said liquid solution is encapsulated.

3. The composition of claim 2, wherein the liquid solution consists essentially of about 5% to about 20% by weight ABT-263 free base, about 15% to about 60% by weight phosphatidylcholine, about 7% to about 30% by weight medium-chain triglycerides, about 7% to about 30% by weight medium-chain mono- and diglycerides, about 7% to about 30% polysorbate 80 surfactant, about 0.02% to about 0.2% by weight sodium or potassium metabisulfite, about 0.003% to about 0.01% EDTA or salt thereof, and about 0.2% to about 0.8% water.

4. The composition of claim 2, comprising a size 0 hard gelatin capsule shell having encapsulated therewithin a liquid solution that comprises about 50 mg ABT-263 free base, about 150 mg phosphatidylcholine, about 75 mg medium-chain triglycerides, about 90 mg medium-chain mono- and diglycerides, about 90 mg polysorbate 80 surfactant, about 0.25 mg sodium or potassium metabisulfite, about 0.025 mg EDTA or salt thereof, and about 2.5 mg water.

* * * * *